US007842705B2

(12) United States Patent
Snyder et al.

(10) Patent No.: US 7,842,705 B2
(45) Date of Patent: *Nov. 30, 2010

(54) CURCUMIN ANALOGS WITH ANTI-TUMOR AND ANTI-ANGIOGENIC PROPERTIES

(75) Inventors: James P. Snyder, Atlanta, GA (US); Matthew C. Davis, Decatur, GA (US); Brian Adams, Decatur, GA (US); Mamoru Shoji, Atlanta, GA (US); Dennis C. Liotta, McDonough, GA (US); Eva M. Ferstl, Chamblee, GA (US); Ustun B. Sunay, Tucker, GA (US)

(73) Assignee: Emory University, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/055,068

(22) Filed: Mar. 25, 2008

(65) Prior Publication Data

US 2008/0234320 A1 Sep. 25, 2008

Related U.S. Application Data

(63) Continuation of application No. 10/690,462, filed on Oct. 21, 2003, now Pat. No. 7,371,766, which is a continuation of application No. 09/729,662, filed on Dec. 4, 2000, now Pat. No. 6,664,272.

(60) Provisional application No. 60/168,913, filed on Dec. 3, 1999.

(51) Int. Cl.
*C07D 211/74* (2006.01)
*C07D 309/30* (2006.01)
*C07D 335/02* (2006.01)
*A61K 31/4412* (2006.01)
*A61K 31/351* (2006.01)
*A61K 31/382* (2006.01)
*A61P 35/00* (2006.01)

(52) U.S. Cl. ............... 514/335; 514/432; 514/451; 546/242; 549/28; 549/416

(58) Field of Classification Search ........... 514/330, 514/432, 451, 445, 460, 335
See application file for complete search history.

(56) References Cited

U.S. PATENT DOCUMENTS

| | | | |
|---|---|---|---|
| 3,114,775 A | 12/1963 | Hughes et al. | |
| 3,515,559 A | 6/1970 | Wayne et al. | |
| 3,897,420 A | 7/1975 | Krapcho et al. | |
| 3,911,129 A | 10/1975 | Krapcho et al. | |
| 3,994,880 A | * 11/1976 | Krapcho et al. | 544/371 |
| 4,127,667 A | 11/1978 | Rovnyak | |
| 4,415,621 A | 11/1983 | Specht et al. | |
| 4,755,450 A | 7/1988 | Sanders et al. | |
| 4,987,057 A | 1/1991 | Kaji et al. | |
| 5,700,804 A | 12/1997 | Collins et al. | |
| 5,811,218 A | 9/1998 | Kaji et al. | |
| 5,852,018 A | 12/1998 | Bryans et al. | |
| 6,022,597 A | 2/2000 | Yan et al. | |
| 2002/0006966 A1 | 1/2002 | Arbiser | |

FOREIGN PATENT DOCUMENTS

JP 03/44643 2/1991
WO WO-01/46110 6/2001

OTHER PUBLICATIONS

Artico, et al., "Geometrically and Conformationally Restrained Cinnamoyl Compounds as Inhibitors of HIV-1 Integrase: Synthesis, Biological Evaluation, and Molecular Modeling," *J. Med. Chem.*, 1998, pp. 3948-3960, vol. 41, No. 21.
Buu-Hoi et al., *Bulletin de la Societe Chimque de France*, 12, 3096-3099, 1964, CA 62: 66406, 1965.
Buu-Hoi et al., *Compt. Rend.* 251, 2725-2727, 1960, CA 55: 112072, 1960.
Chen et al.,*Thromb, Haemost.* 86(1): 334-345, 2001.
Cremlyn et al., "The Synthesis and Chlorosulfonation of Some Diarylidene and Heteroarylidene Ketones with Varying Alicyclic Ring Size", *Phosphorus, Sulfur, and Silicon*, 1995, pp. 205-217, vol. 107.
Desiraju et al., "A Convenient Preparation of Substituted 2,5-Dibenzylidenecyclopent-3-en-1-ones," *Indian Journal of Chemistry*, 1988, pp. 953-954, vol. 27B, No. 10.
Dimmock et al., "Evaluation of Some N-Acyl Analogues of 3,5-Bis(arylidene)-4-Piperidones for Cytotoxic Activity," *Drug Design and Discovery*, 1992, vol. 8, pp. 291-299.
Dimmock et al., "Cytotoxic Evaluation of Some 3,5-Diarylidene-4-piperidones and Various Related Quaternary Ammonium Compounds and Analogs," *Journal of Pharmaceutical Sciences*, 1994, pp. 1124-1130, vol. 83, No. 8.
Dinkova-Kostova, et al., "Chemoprotective Properties of Phenylpropenoids, Bis(benzylidene)cycloalkanones, and Related Michael Reaction Acceptors: Correlation of Potencies as Phase 2 Enzyme Inducers and Radical Scavengers," *J. Med. Chem.*, 1998, pp. 5287-5296, vol. 41, No. 26.
El-Subbagh, et al., "Synthesis and Biological Evaluation of Certain α,β-Unsaturated Ketones and Their Corresponding Fused Pyridines as Antiviral and Cytotoxic Agents," *J. Med. Chem.*, 2000, pp. 2915-2921, vol. 43, No. 15.
Fujisaki, et al., JP 62225562, 1988 (CA 108:77360).
Gutkowska, *Poloniae Pharmaceutica*, 1973, pp. 361-364, vol. 30, No. 4.
Gutkowska, et al., *Acta Poloniae Pharmaceutica*, 1985, pp. 437-441, vol. 42, No. 5 (CA 107:115819).
Gutkowska, et al., *Acta Poloniae Pharmaceutica*, 1989, pp. 212-218, vol. 46, No. 3 (CA 112:216649).
Hammam, et al., "Synthesis and Anti-Cancer Activity of Pyridine and Thiazolopyrimidine Derivatives Using 1-Ethylpiperidone as a Synthon," *Indian J. Chem.*, 2001, pp. 213-221, vol. 40B.
Katritzky et al., "Bridged Cyanine Dyes. Part 3 [1]. Zwitterionic Bis-4-pyridyl and Cationic Bis-dimethylanilino Derivatives,"*Journal of Heterocyclic Chemistry*, 1988, pp. 1321-1325, vol. 25, No. 5.

(Continued)

*Primary Examiner*—Venkataraman Balasubramanian
(74) *Attorney, Agent, or Firm*—Alston & Bird LLP

(57) ABSTRACT

The present invention is directed to curcumin analogs exhibiting anti-tumor and anti-angiogenic properties, pharmaceutical formulations including such compounds and methods of using such compounds.

30 Claims, 5 Drawing Sheets

OTHER PUBLICATIONS

Keinan, et al., *J. Org. Chem.*, 1983, pp. 5302-5309, vol. 48, No. 26.

Leonard et al., "γ-Pyrones by Isomerizaton. Substituted 3,5-Dibenzy1-4H-pyran-4-ones," *Journal of the American Chemical Society*, 1957, pp. 156-160, vol. 79, No. 1.

Li, et al., "Samarium (III) Iodide Promoted Preparation of α,α'—bis(substituted benzylidene) cyclohexanones from Benzaldehydes and Cyclohexanone," *J. Chem, Research (S)*, 2000, pp. 580-581.

Mahfouz, et al., "Synthese mehrfach oxigenierter 2-Hydroxyxanthone," *Arch. Pharm. (Weinheim)*, 1990, pp. 163-169, vol. 323.

Nakano, et al., "A Convenient Synthesis of α,α'—Bis(substitutedbenzylidene)cycloalkanones," *Chemistry Letters*, 1993, pp. 2157-2158.

Ojima, et al., *Bull. Chem. Soc. Jpn.*, 1977, pp. 1522-1526, vol. 50, No. 6 (CA 87:20055).

Pivnenko, et al., *Zh. Org. Khim*, 1972, pp. 1096-1102, vol. 42, No. 5 (CA 84:513251).

Pivnenko, et al., *Zh. Org. Khim*, 1975, pp. 2527-2533, vol. 11, No. 12 (CA 84:73234).

Shoppee, et al., *J. Chem. Soc. Perkin Trans I*, 1977, pp. 1028-1030, vol. 9 (CA 87:102029).

Sun, et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," *J. Med. Chem.*, 1999, pp. 5120-5130, vol. 42, No. 25.

Sun, et al., "Identification of Substituted 3-[(4,5,6,7-Tetrahydro-1H-indo1-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," *J. Med. Chem.*, 2000, pp. 2655-2663, vol. 43, No. 14.

Sun, et al., "Synthesis and Biological Evaluations of 3-Substituted Indolin-2-ones: A Novel Class of Tyrosine Kinase Inhibitors That Exhibit Selectivity toward Particular Receptor Tyrosine Kinases," *J. Med. Chem.*, 1998, pp. 2588-2603, vol. 41, No. 14.

Teuscher, "Potentiell antiangiogene Substanzen aus der Gruppe der α, α'—Bis(amidinobenzyl)cycloalkanon-Derivate and α-(Arylsulfonylamino)-ω-phenylcarbonsäure-4- amidinoanilide," *Pharmazie*, 1987, pp. 109-110, vol. 42, H.2.

Thaloor, et al., "Inhibition of Angiogenic Differentiation of Human Umbilical Vein Endothelial Cells by Curcumin," *Cell Growth & Differentiation*, 1998, pp. 305-312, vol. 9.

Vieth, et al., "DoMCoSAR: A Novel Approach for Establishing the Docking Mode That Is Consistent with the Structure-Activity Relationship. Application to HIV-1 Protease Inhibitors and VEGF Receptor Tyrosine Kinase Inhibitors", *J. Med. Chem.*, 2000, pp. 3020-3032, vol. 43, No. 16.

Wiemer et al., "Vidalols A and B, New Anti-Inflammatory Bromophenols from the Caribbean Marine Red Alga *Vidalia obtusaloba*," *Experientia*, 1991, pp. 851-853, vol. 47.

Zheng, et al., *Zhongguo Yiyao Gonye Zazhi*, 1997, p. 230231, vol. 28, No. 5 (CA 115:102878).

\* cited by examiner

Relationship between cell viability and VEGF production after treatment with curcumin analogs. RPMI 7951 human melanoma cells were treated with analogs for three days at concentrations of 5μM (A) or 20μM (B). Series II analogs (EF 15, A279L, and A279U) inhibit VEGF production without affecting viability.

Inhibition of human melanoma cell growth by curcumin analogs. Neutral Red Assay was used to determine the viability of RPMI 7951 cells treated for three days with various concentrations of either known (A) or novel (B) compounds.

Inhibition of human breast cancer cell proliferation by curcumin analogs. Neutral Red Assay was used to determine the viability of MDA-MB-231 (A) or MDA-MB-435 (B) cells treated for three days with novel compounds or taxol.

Curcumin analogs inhibit transformed murine endothelial cell proliferation. Neutral Red Assay was used to determine the viability of SVR cells treated for three days with various concentrations of either known (A) or novel (B) compounds.

Inhibition of human endothelial cell growth by curcumin analogs. Neutral Red Assay was used to determine the viability of HUVECS treated for three days with various concentrations of either known (A) or novel (B) analogs.

CURCUMIN ANALOGS WITH ANTI-TUMOR AND ANTI-ANGIOGENIC PROPERTIES

CROSS-REFERENCE TO RELATED APPLICATIONS

This application is a continuation of U.S. application Ser. No. 10/690,462, filed 5 Oct. 21, 2003, now U.S. Pat. No. 7,371,766, which is a continuation of U.S. application Ser. No. 09/729,662, filed Dec. 4, 2000, now U.S. Pat. No. 6,664,272, which claims the benefit of U.S. Provisional No. 60/168,913, filed Dec. 3, 1999, all of which are incorporated by reference herein in its entirety.

FIELD OF THE INVENTION

The invention relates to compounds useful for the treatment of cancer, and in particular to compounds exhibiting anti-tumor and anti-angiogenic properties and methods for using such compounds.

BACKGROUND OF THE INVENTION

Tissue factor (TF) is a sedimentable, integral membrane receptor protein with an estimated molecular weight of 42-47 kDa. Peritumor fibrin deposition, which is characteristic of most types of human cancer, is the result of the local expression of potent procoagulants like tissue factor (TF) in tumor cells, tumor-associated macrophages (TAMs) and tumor-associated vascular endothelial cells (VECs). In addition to the importance of TF expression in the pathogenesis of the thrombotic complications common to cancer patients, increasing evidence links TF expression to the regulation of tumor angiogenesis, growth and metastasis. For example, angiogenesis in vivo is inhibited by TF antisense. Further, murine tumor cells transfected to overexpress TF enhance vascular permeability factor (VEGF) transcription and translation. Conversely, tumor cells transfected with TF antisense reduce VEGF transcription and translation. VEGF acts specifically on VECs to promote vascular permeability, endothelial cell growth and angiogenesis, and has been shown to induce expression of TF activity in VECs and monocytes and is chemotactic for monocytes, osteoblasts and VECs. Expression of TF and VEGF in cancer cells is further enhanced under hypoxic condition. Thus, there is evidence to suggest that TF is a key molecule participating in the regulation of VEGF synthesis and, hence, tumor angiogenesis in cancer.

Relatively few compounds exhibiting anti-angiogenic properties useful in the treatment of cancer have been investigated. Curcumin (diferuloylmethane), the aromatic yellow pigment in curry, turmeric and mustard, is known to have anti-angiogenic, anti-tumor, and anti-tumor promoting properties. In addition, curcumin exhibits numerous other therapeutic effects, including anti-oxidative, anti-thrombotic, anti-inflammatory, anti-cholesterol and anti-diabetic properties. Two other compounds that have received considerable attention are genistein, a soybean-derived isoflavone tyrosine kinase C inhibitor, and linomide, a quinoline-3-carboxaminde. Certain flavonoids, such as apigenin, have been shown to be more potent inhibitors of cell proliferation and in vitro angiogenesis than genistein. There remains a need in the art for compounds that exhibit anti-tumor and anti-angiogenic properties for use in cancer therapy.

SUMMARY OF THE INVENTION

The present invention provides a group of curcumin analogs that inhibit TF expression and VEGF expression in cancer cells and in vascular endothelial cells in the tumor microenvironment, thereby blocking tumor angiogenesis and growth, without exhibiting a high level of toxicity with regard to normal vascular endothelial cells. The anti-angiogenic and anti-tumor compounds of the present invention can be useful in the treatment of any condition benefiting from angiogenesis inhibition, such as cancer.

In one aspect, the present invention provides compounds of Formula (I) below.

In another aspect, the present invention provides a pharmaceutical formulation comprising a compound of Formula (I) or Formula (II) below in a pharmaceutically acceptable carrier.

In a third aspect, the present invention provides a method of treating cancerous tissue in a subject, comprising administering an effective amount of a compound of Formula (I) or Formula (II) to the subject. Preferably, the compound is administered in a pharmaceutically acceptable carrier. The effective amount is preferably an amount sufficient to inhibit VEGF or TF production in the cancerous tissue.

BRIEF DESCRIPTION OF THE DRAWINGS

Figure 1A:
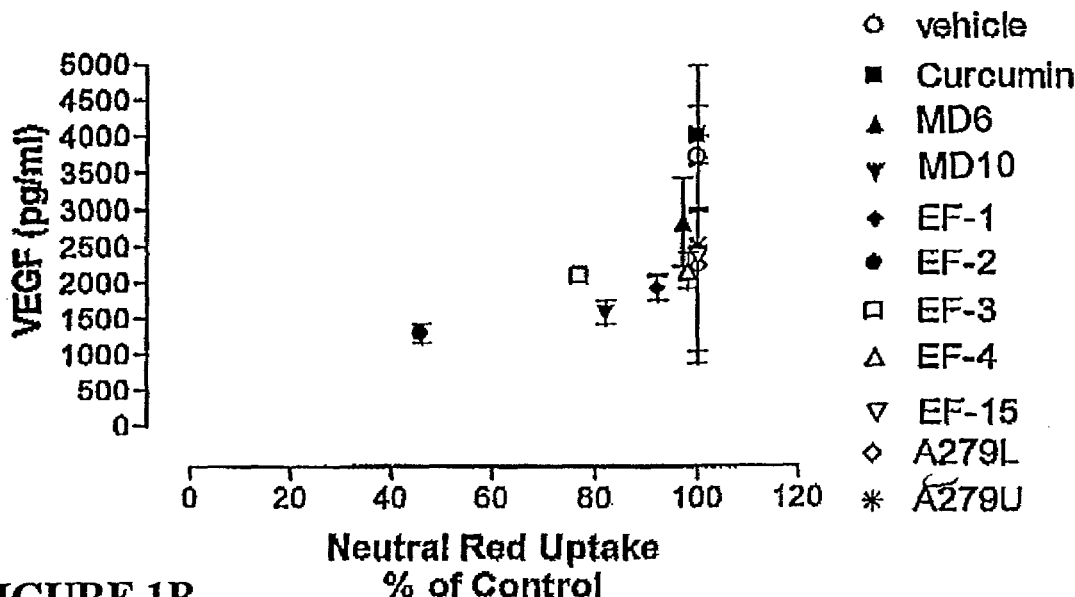
Figure 1B:
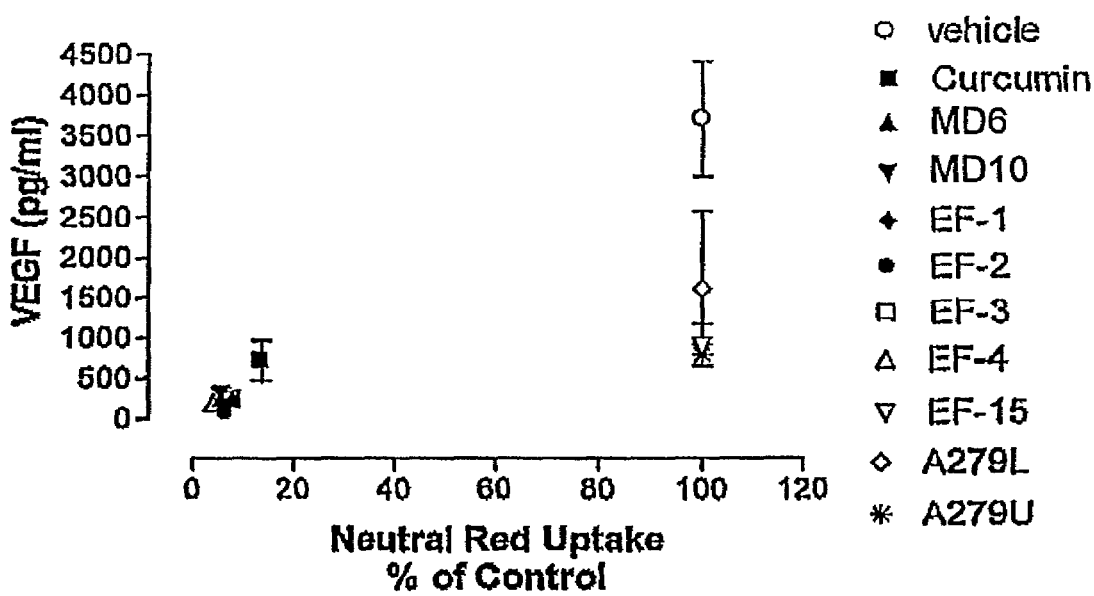
Figure 2A:
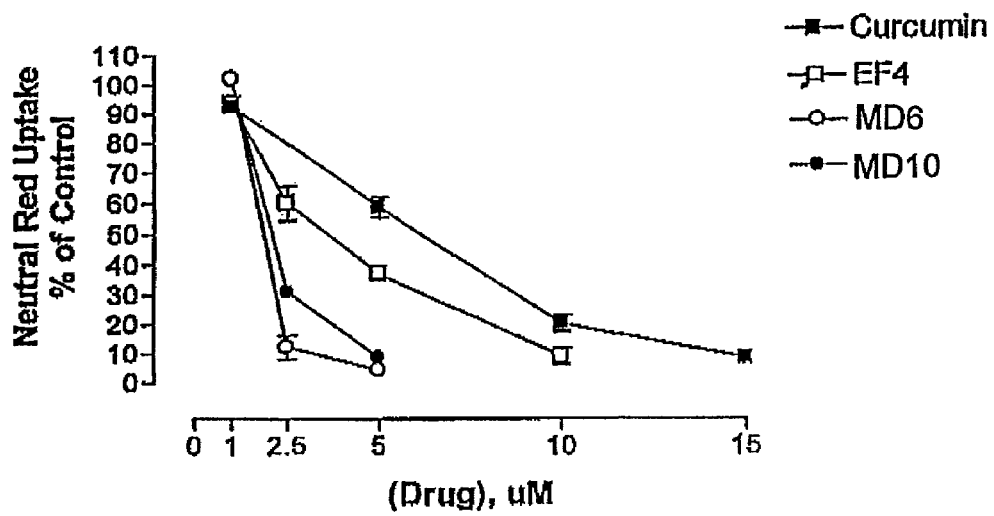
Figure 2B:
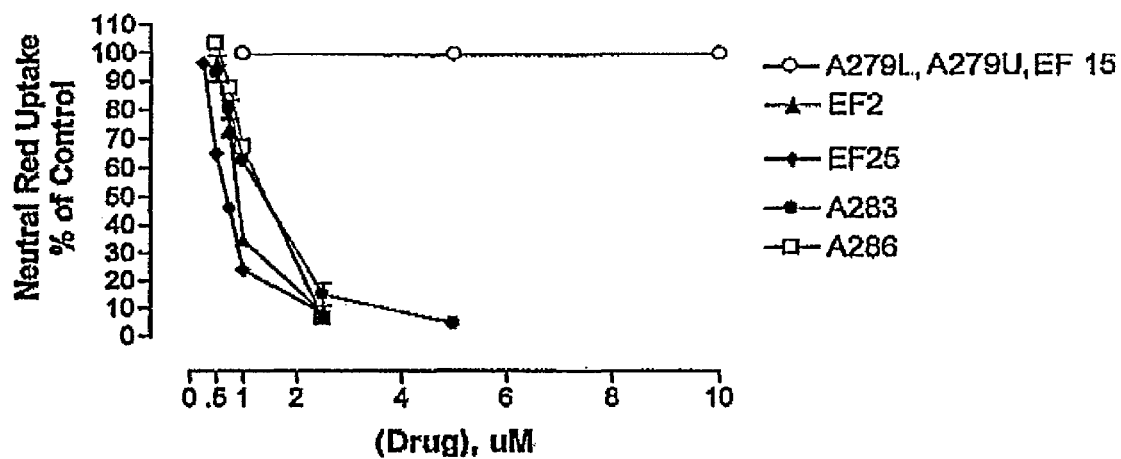
Figure 3A:
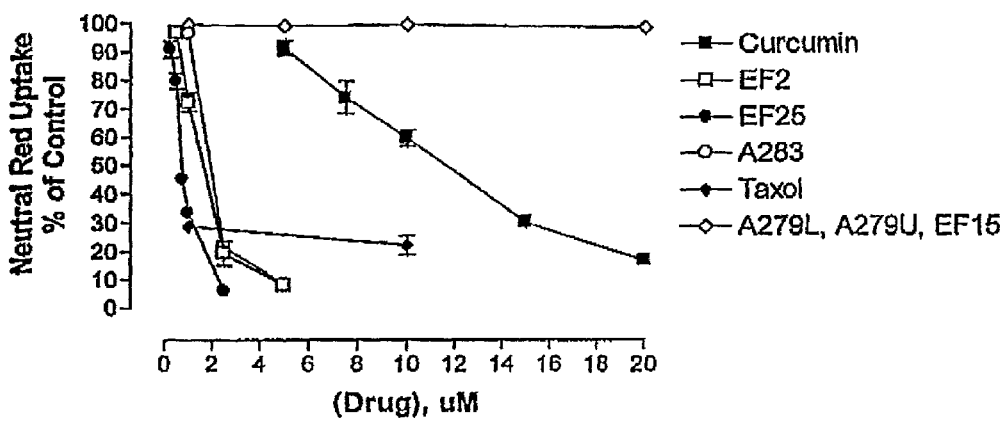
Figure 3B:
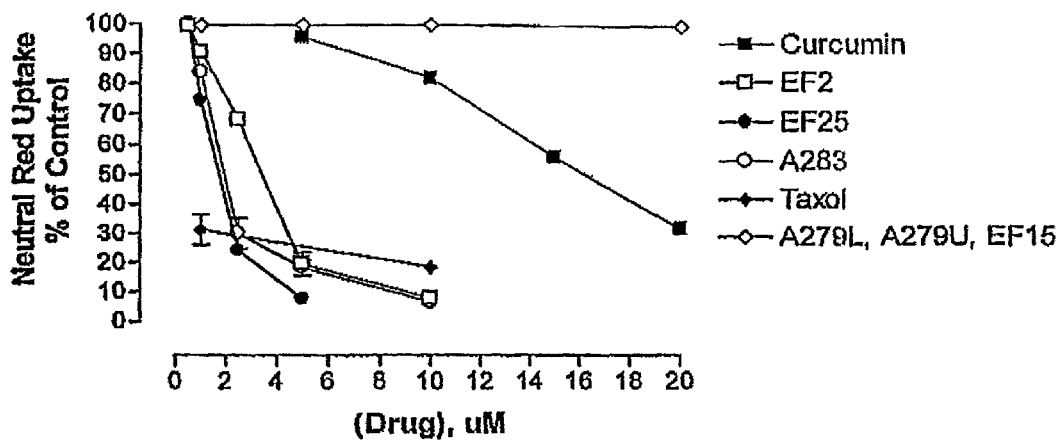
Figure 4A:
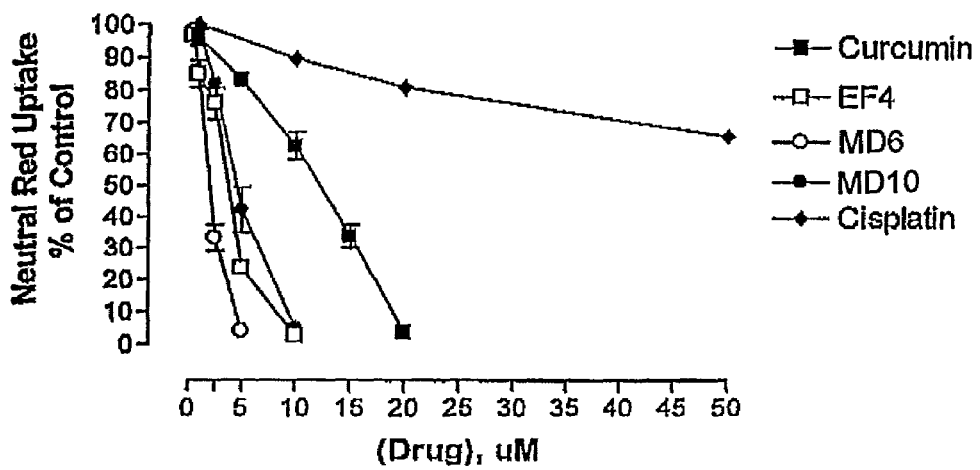
Figure 4B:
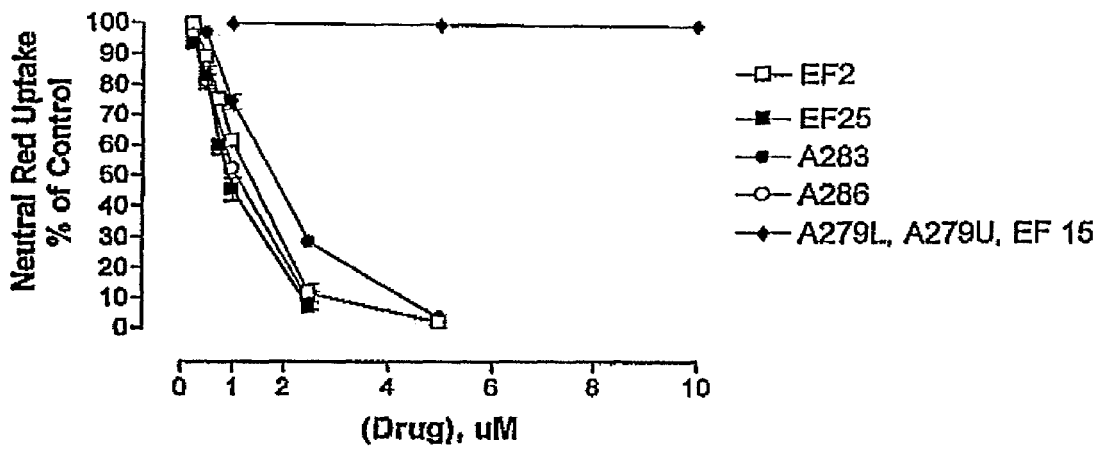
Figure 5A:
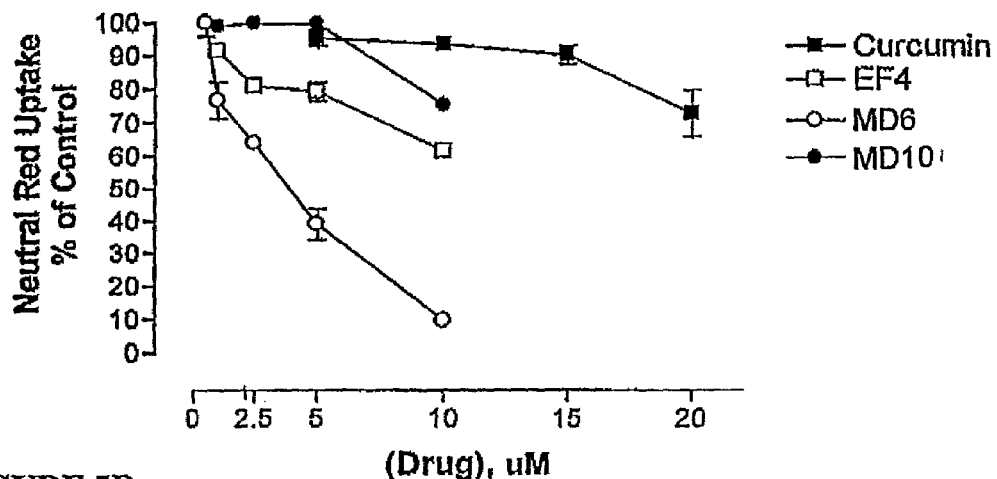
Figure 5B:
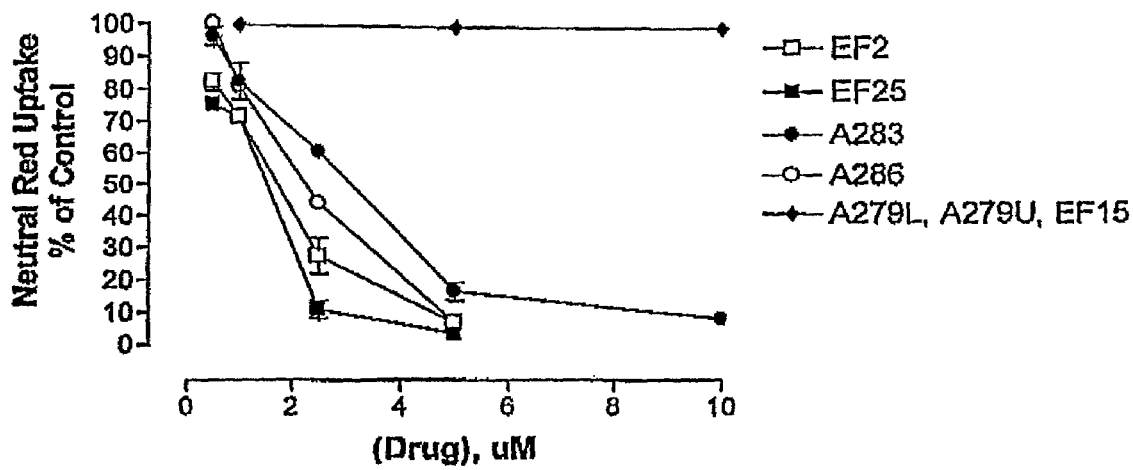

Having thus described the invention in general terms, reference will now be made to the accompanying drawings, wherein:

FIGS. 1A and 1B graphically illustrate the relationship between cell viability and VEGF production of human melanoma cells after treatment with the compounds of the present invention at two concentrations;

FIGS. 2A and 2B graphically illustrate the effect of known compounds and the compounds of the present invention on human melanoma cell viability;

FIGS. 3A and 3B graphically illustrate the effect of known compounds and the compounds of the present invention on human breast cancer cell viability;

FIGS. 4A and 4B graphically illustrate the effect of known compounds and the compounds of the present invention on transformed murine endothelial cell viability; and FIGS. 5A and 5B graphically illustrate the effect of known compounds and the compounds of the present invention on human endothelial cell viability.

DETAILED DESCRIPTION OF THE INVENTION

The present invention will be described more fully hereinafter, including preferred embodiments thereof. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "compound" is intended to refer to a chemical entity, whether in the solid, liquid or gaseous phase, and whether in a crude mixture or purified and isolated. The terms "alkyl," "alkene," and "alkoxy" include straight chain and branched alkyl, alkene, and alkoxy, respectively. The term "lower alkyl" refers to C1-C4 alkyl. The term "alkoxy" refers to oxygen substituted alkyl, for example, of the formulas —OR or —ROR$^1$, wherein R and R$^1$ are each independently selected alkyl. The terms "substituted alkyl" and "substituted alkene" refer to alkyl and alkene, respectively, substituted with one or more non-interfering substituents, such as but not limited to, C3-C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like. The term "halogen" includes fluorine, chlorine, iodine and bromine.

"Aryl" means one or more aromatic rings, each of 5 or 6 carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents.

"Heteroaryl" is an aryl group containing from one to four N, O, or S atoms(s) or a combination thereof, which heteroaryl group is optionally substituted at carbon or nitrogen atom(s) with C1-6 alkyl, —CF$_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1, 2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms.

"Substituted heteroaryl" is heteroaryl having one or more non-interfering groups as substituents.

"Heterocycle" or "heterocyclic" means one or more rings of 5, 6 or 7 atoms with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" is heterocycle having one or more side chains formed from non-interfering substituents.

"Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_7$-$C_{12}$ aralkyl, $C_7$-$C_{12}$ alkaryl, $C_3$-$C_{10}$ cycloalkyl, $C_3$-$C_{10}$ cycloalkenyl, phenyl, substituted phenyl, toluoyl, xylenyl, biphenyl, $C_2$-$C_{12}$ alkoxyalkyl, $C_7$-$C_{12}$ alkoxyaryl, $C_7$-$C_{12}$ aryloxyalkyl, $C_6$-$C_{12}$ oxyaryl, $C_1$-$C_6$ alkylsulfinyl, $C_1$-$C_{10}$ alkylsulfonyl, —(CH$_2$)$_m$—O—(C$_1$-C$_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C$_1$-C$_{10}$ alkyl), —C(O)—(C$_1$-C$_{10}$ alkyl), $C_2$-$C_{10}$ thioalkyl, —C(O)O—(C$_1$-C$_{10}$ alkyl), —OH, —SO$_2$, =S, —COOH, —NR$_2$, carbonyl, —C(O)—(C$_1$-C$_{10}$ alkyl)-CF$_3$, —C(O)—CF$_3$, —C(O)NR$_2$, —(C$_1$-C$_{10}$ alkyl)-S—(C$_6$-C$_{12}$ aryl), —C(O)—(C$_6$-C$_{12}$ aryl), —(CH$_2$)$_m$—O—(CH$_2$)$_m$—O—(C$_1$-C$_{10}$ alkyl) wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

The present invention provides compounds of Formula (I)

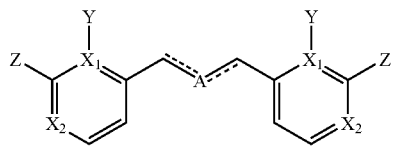

wherein:
Y is OH, halogen, or CF$_3$;
Z is H, OH, OR$_1$, halogen, or CF$_3$;
X$_1$ and X$_2$ are independently C or N; and
A is selected from the group consisting of:

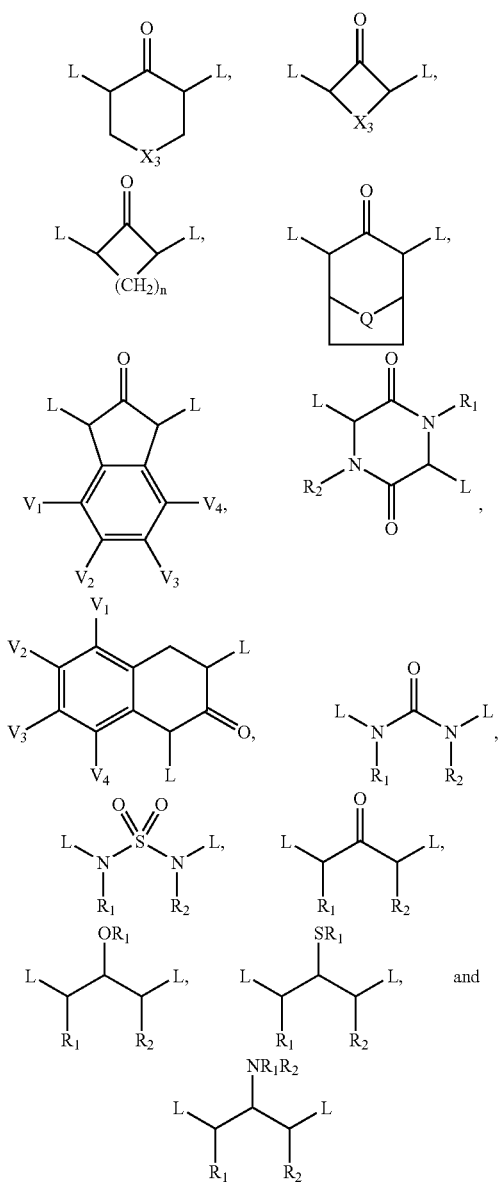

wherein n is 1-8; X$_3$ is O, S, SO, SO$_2$, NH, or NR$_1$; Q is NH or NR$_1$; and V$_{1-4}$ are each independently OH, OR$_2$, or halogen; R$_1$ and R$_2$ are independently H, alkyl, substituted alkyl, aryl, substituted aryl, heteroaryl, substituted heteroaryl, heterocycle, substituted heterocycle, acyl, alkoxycarbonyl, aminocarbonyl, alkylaminocarbonyl or dialkylaminocarbonyl; the dashed lines indicate the presence of optional double bonds; and L is the point of bonding of A to the compound structure, with the proviso that Z is not H when Y is OH, Cl or Br and A is

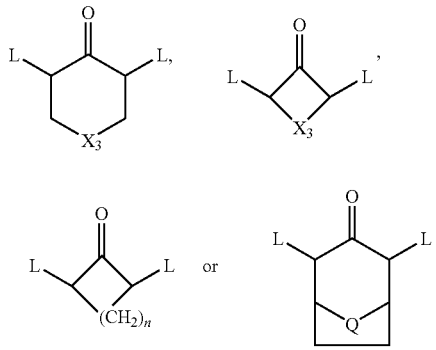

and pharmaceutically acceptable salts thereof.

The present invention also provides a method of treating cancerous tissue in a subject, such as a human or other mammal, comprising administering to the subject an effective amount of a compound of Formula (I) above or a compound of Formula (II)

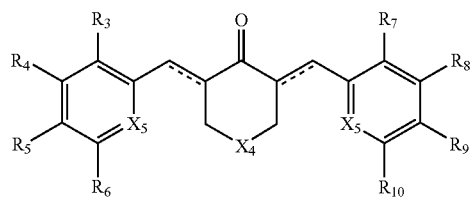

wherein:

$X_4$ is $(CH_2)_m$, O, S, SO, $SO_2$, or $NR_{12}$, where $R_{12}$ is H, alkyl, substituted alkyl, acyl, alkoxycarbonyl, aminocarbonyl, alkylaminocarbonyl or dialkylaminocarbonyl;

m is 1-7;

each $X_5$ is independently N or C—$R_{11}$;

and each $R_3$-$R_{11}$ are independently H, halogen, hydroxyl, alkoxy, $CF_3$, alkyl, substituted alkyl, alkenyl, alkynyl, cycloalkyl, substituted cycloalkyl, aryl, substituted aryl, alkaryl, arylalkyl, heteroaryl, substituted heteroaryl, heterocycle, substituted heterocycle, amino, alkylamino, dialkylamino, carboxylic acid, carboxylic ester, carboxamide, nitro, cyano, azide, alkylcarbonyl, acyl, or trialkylammonium; and the dashed lines indicate optional double bonds;

with the proviso that when $X_4$ is $(CH_2)_m$, m is 2-6, and each $X_5$ is C—$R_{11}$, $R_3$-$R_{11}$ are not alkoxy, and when $X_4$ is $NR_{12}$ and each $X_5$ is N, $R_3$-$R_{10}$ are not alkoxy, alkyl, substituted alkyl, alkenyl, alkynyl, cycloalkyl, substituted cycloalkyl, aryl, substituted aryl, alkaryl, arylalkyl, heteroaryl, substituted heteroaryl, amino, alkylamino, dialkylamino, carboxylic acid, or alkylcarbonyl.

The present invention includes all stereoisomeric configurations of the compounds of Formula (I) and Formula (II), including both optical isomers, such as enantiomers and diastereoisomers, and geometric (cis-trans) isomers.

Examples of the compounds of the present invention include, but are not limited to:

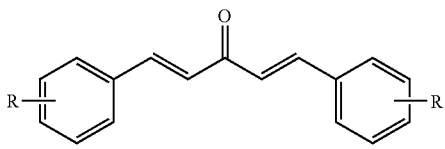

(EF2)   R = 2-OH
(EF3)   R = 3-OH
(EF1)   R = 4-OH
(EF8)   R = 2-F
(EF9)   R = 2,4-F
(EF10) R = 3,4-F
(EF23) R = 2,6-F
(MD6)  R = 3,4-(OMe)
(EF16) R = 2-OMe
(EF17) R = 3-OMe
(EF18) R = 4-OMe

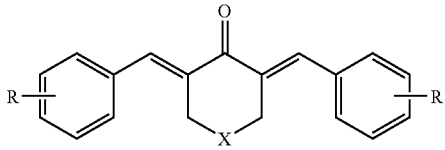

(EF4)   X = C, R = 2-OH
(EF31) X = C-1, R = 2-OH
(EF25) X = O, R = 2-OH
(EF29) X = O, R = 2-F
(EF30) X = O, R = 2,4-F
(EF36) X = O, R = 3,4(OMe)
(EF28) X = O, R = 2-OMe
(EF27) X = O, R = 4-OMe
(EF34) X = NMe, R = 2-OH
(EF33) X = NMe, R = 2-F
(EF47) X = NMe, R = 2,4-F
(EF35) X = NMe, R = 3,4-(OMe)
(EF24) X = $NH_2OAc$, R = 2-F
(EF26) X = $NH_2Cl$, R = H

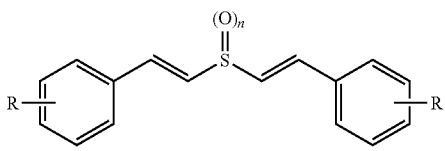

(EF15) n = 0, R = H
(EF13) n = 1, R = H, (E, E)
(EF14) n = 1, R = H, (E, Z)
(EF11) n = 2, R = 2-OH
(EF12) n = 2, R = H

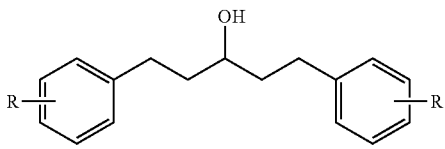

(EF32)    R = 2-OH
(EF48)    R = 2-F
(EF19)    R = 2,4-$F_2$
(EF20)    R = 3,4-$F_2$
(MD279L) R = 3,4-(OMe)

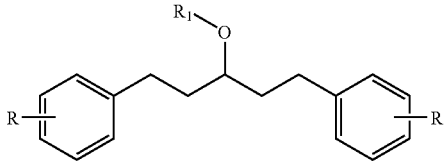

(EF37)   $R_1$ = Me, R = 3,4-F
(MD38) $R_1$ = Me, R = 3,4-(OMe)
(EF44)   $R_1$ = Pr, R = 3,4-(OMe)

-continued
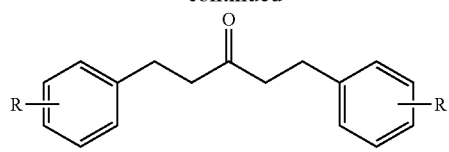
(EF21)  R = 2,4-F
(EF22)  R = 3,4-F
(MD279U) R = 3,4-(OMe)
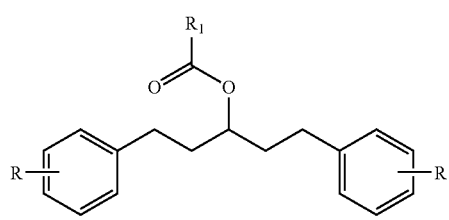
(EF46) R₁ = CH₂Br,  R = 3,4-(OMe)
(EF40) R₁ = Et,      R = 3,4-F
(EF41) R₁ = Et,      R = 3,4-(OMe)
(EF49) R₁ = Ph,      R = 2-F
(EF39) R₁ = Ph,      R = 3,4-(OMe)
(EF45) R₁ = morph.   R = 3,4-(OMe)
(EF43) R₁ = menth.,  R = 3,4-(OMe)
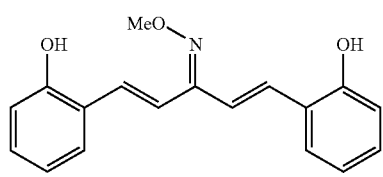
(EF6)
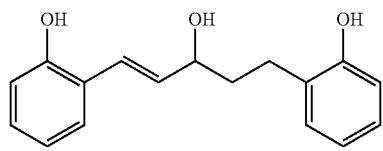
(EF5)
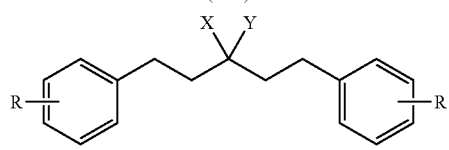
(EF42) R = 3,4-(OMe)  X = Cl
                      Y = H
(EF50) R = 3,4-(OMe)  X = OH
                      Y = Me
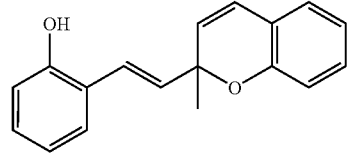
(EF7)
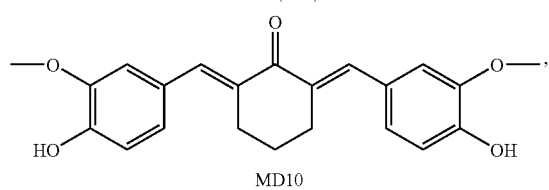
MD10
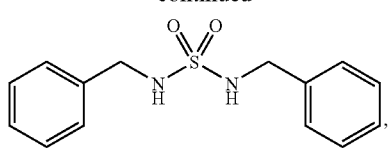
MD272
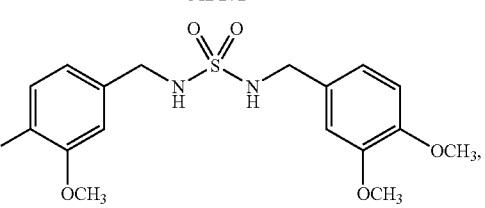
MD277a
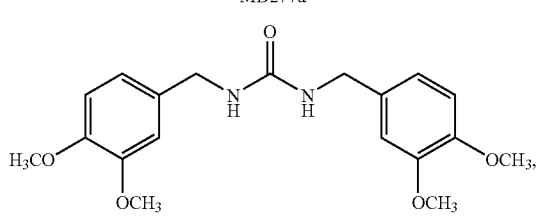
MD277b
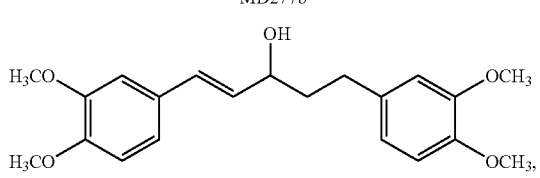
MD239
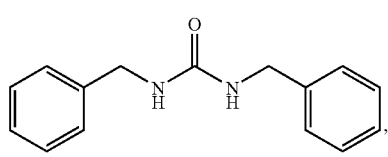
MD271a
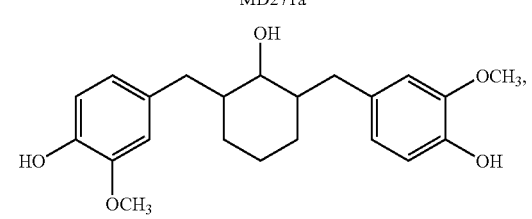
MD231L
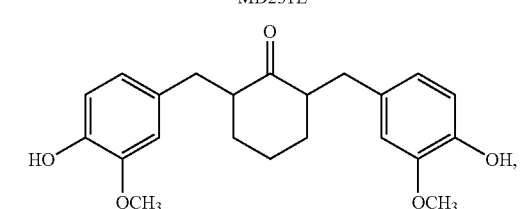
MD231U
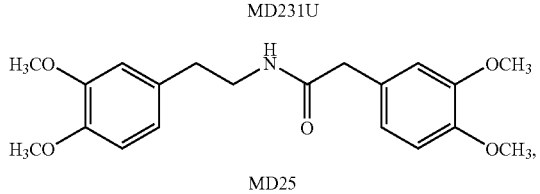
MD25

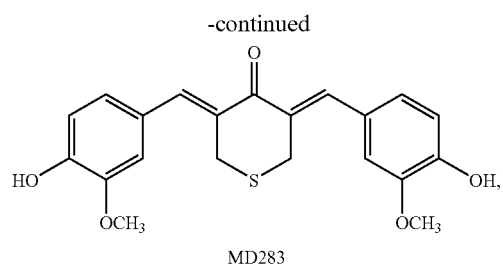
MD283
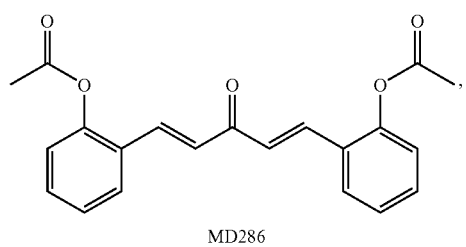
MD286
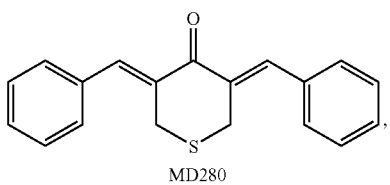
MD280
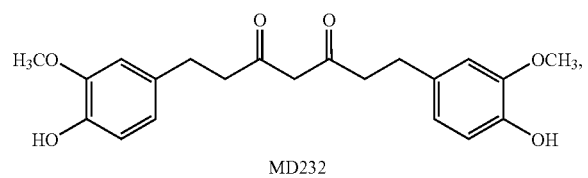
MD232
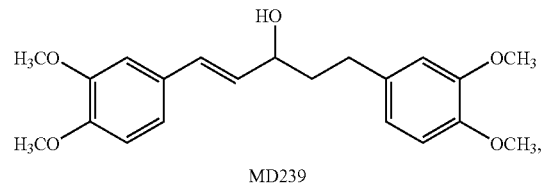
MD239
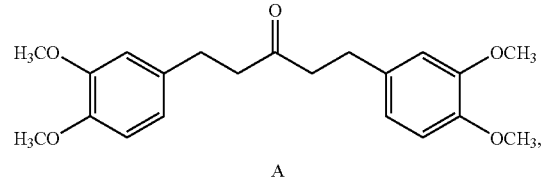
A
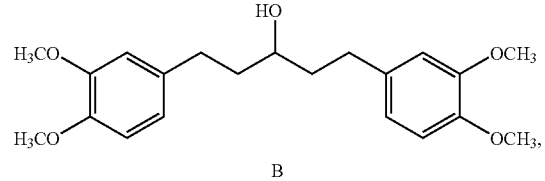
B
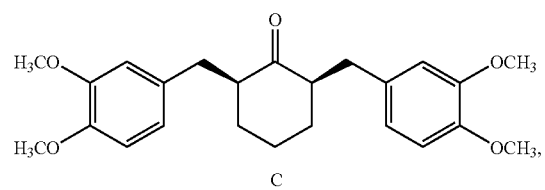
C
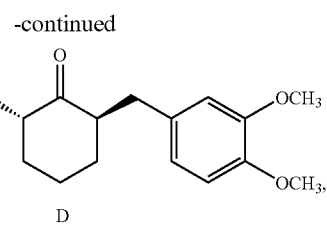
D
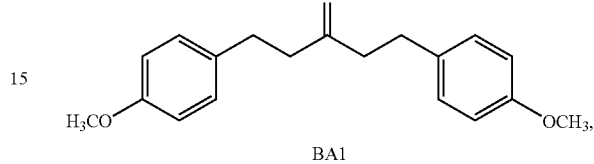
BA1
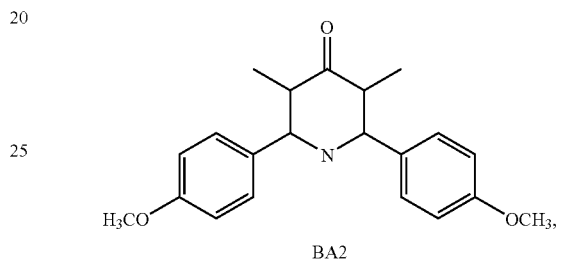
BA2
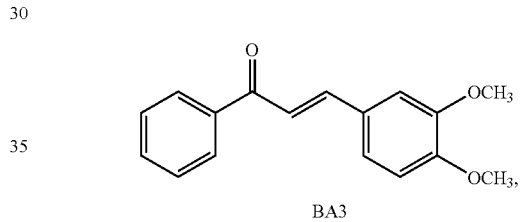
BA3
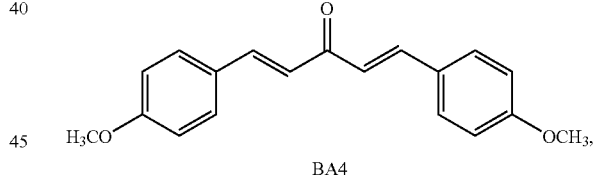
BA4
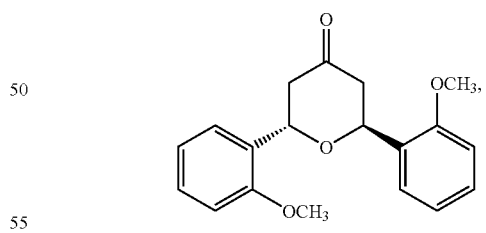
BA6
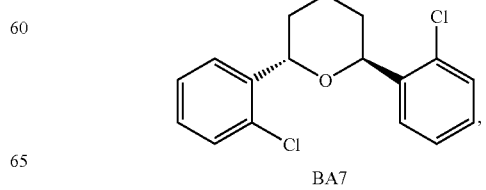
BA7

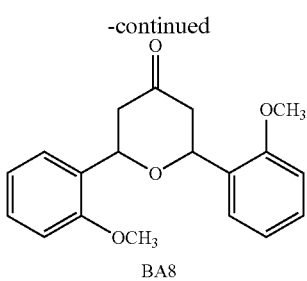

BA8 and the like and pharmaceutically acceptable salts thereof. Additional exemplary compounds are given in the appended examples.

The compounds of the present invention may be prepared according to methods known in the art, particularly in light of the disclosure and examples set forth herein. The starting materials used to synthesize the compounds of the present invention are commercially available or capable of preparation using methods known in the art. For example, some compounds of the present invention may be prepared by reaction of an aromatic aldehyde, such as hydroxybenzaldehyde or fluoro-substituted benzaldehyde, with a ketone, such as acetone, cyclohexanone, cyclopentanone, tetrahydro-4-H-pyran-4-one, N-methyl-4-piperidone, piperidin-4-one, and the like, under basic aldol condensation conditions. Similarly, other compounds of the present invention may be prepared by reaction of an alkoxy-substituted benzaldehyde or anisaldehyde with a ketone. As would be understood, the actual ketone or aldehyde utilized will depend on the type and position of the substituents of the desired final compound. The salts of the present invention may be prepared, in general, by reaction of a compound of the invention with the desired acid or base in solution. After the reaction is complete, the salts can be crystallized from solution by the addition of an appropriate amount of solvent in which the salt is insoluble.

The compounds of Formula (I) or Formula (II) can have pharmaceutical activity and can be useful in the treatment of a subject suffering from one or more conditions that would benefit from inhibition of angiogenesis. For example, the compounds of the present invention can be used in the treatment of cancerous tissue and the tumors associated therewith, including breast, colon, prostate and skin cancer. In addition, the compounds of the present invention can be useful for mediating inflammation, rheumatoid arthritis and certain forms of diabetes. Subjects which can be treated include animal subjects, typically vertebrates, including both mammalian (e.g., human, cat, dog, cow, horse, sheep, pig, monkey, ape, etc.) and avian subjects (e.g., chicken, turkey, duck, goose, quail, pheasant, etc.). It is believed, for example, that administering an effective amount of a compound of Formula (I) or Formula (II) to a subject can result in inhibition of angiogenesis in cancerous tissue. Thus, the present invention can provide methods for treating tumor-bearing subjects in which the compounds of the invention are administered to the subject in need of such treatment in an amount effective and in a manner effective to combat such tumors, for example, by virtue of inhibition of angiogenesis within the tumor. The anti-angiogenesis effect is believed to result, at least in part, from inhibition of TF and/or VEGF production in the tumor. In addition, it is believed that the compounds of the present invention can be used as a prophylactic treatment to prevent certain types of inflammatory skin conditions including, but not limited to, dermatitis and mild cases of skin cancer.

The compounds of Formula (I) or Formula (II) may be administered per se or in the form of a pharmaceutically acceptable salt. When used in medicine, the salts of the compounds of Formula (I) or Formula (II) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of a compound of Formula (I) or Formula (II) with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of the carboxylic acid group.

Thus the present invention also provides pharmaceutical formulations or compositions, both for veterinary and for human medical use, which comprise the compounds of Formula (I) or Formula (II) or a pharmaceutically acceptable salt thereof with one or more pharmaceutically acceptable carriers thereof and optionally any other therapeutic ingredients, such as other chemotherapeutic agents. The carrier(s) must be pharmaceutically acceptable in the sense of being compatible with the other ingredients of the formulation and not unduly deleterious to the recipient thereof.

The compositions includes those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier or both, and then, if necessary, shaping the product into desired formulations.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parental administration conveniently comprise a sterile aqueous preparation of the active compound, which can be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Further, the present invention provides liposomal formulations of the compounds of Formula (I) or Formula (II) and salts thereof. The technology for forming liposomal suspensions is well known in the art. When the compound of Formula (I) or Formula (II) or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer that forms the structure of the liposome. In either instance, the liposomes that are produced may be reduced in size, as through the use of standard sonication and homogenization techniques. The liposomal formulations containing the compounds of Formula (I) or Formula (II) or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula (I) or Formula (II) or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts.

In addition to the aforementioned ingredients, the compositions of the invention may further include one or more accessory ingredient(s) selected from the group consisting of diluents, buffers, flavoring agents, binders, disintegrants, surface active agents, thickeners, lubricants, preservatives (including antioxidants) and the like.

Preferably, for purposes of cancer therapy, a compound of Formula (I) or Formula (II) is administered to the subject in an amount sufficient to inhibit production of TF or VEGF, thereby inhibiting angiogenesis. However, the therapeutically effective dosage of any specific compound will vary somewhat from compound to compound, patient to patient, and will depend upon the condition of the patient and the route of delivery. As a general proposition, a dosage from about 0.5 to about 20 mg/kg body weight, preferably from about 1.0 to about 5.0 mg/kg, will have therapeutic efficacy. When administered conjointly with other pharmaceutically active agents, even less of the compounds of Formula (I) or Formula (II) may be therapeutically effective. The compound of Formula (I) or Formula (II) may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

For the following examples, RPMI-7951 human melanoma, MDA-MB-231 and MDA-MB-435 human breast cancer cell lines were purchased from American Type Cell Collection (Rockville, Md.). HUVECs were obtained from the Department of Dermatology, Emory University. Murine endothelial cells infected with simian virus 40 (SV40) large T antigen and activated H-ras (SVR), were a kind gift from Dr. Jack Arbiser at Emory. RPMI-7951, MDA-MB-231 and MDA-MB-435 cell lines were cultured in MEM-alpha medium (GIBCO-BRL, Long Island, N.Y.) containing 10% fetal bovine serum (RPMI-7951, MDA-MB-231) or 5% FBS (MDA-MB-435) at 37° C. and under 5% $CO_2$/95% air. SVR cells were cultured in DMEM (Mediatech cellgro) containing 10% FBS and 2 mM L-glutamine. Complete HUVEC media was a gift from the Cell Culture Center in the Department of Dermatology, Emory University. The cells were cultured in 48 well plates in all of the experiments described.

Neutral Red Assay was utilized to determine the effect of the compounds of the present invention on cell viability. Neutral Red was purchased from GIBCO-BRL (Long Island, N.Y.). Cells were plated at a concentration of 20,000 cells/well and cultured overnight. Compounds or vehicle (DMSO 0.1%) were then added and the plates were incubated for 72 hours. Supernatant from each well was either aspirated or collected and media containing Neutral Red (GIBCO-BRL, Long Island, N.Y.) at a concentration of 15 µl/ml was then added to each well. The plates were then incubated at 37° C. for 30 minutes. Next, the cells were washed with twice with PBS and alcoholic-HCl (0.5N—HCl/35% ethanol) was added to each well. The plates were then placed on a plate shaker until all residues were solubilized (pink color). The solubilized mixtures were then transferred to a 96 well plate and the absorbances were read on a micro-test plate reader at a wavelength of 570 nM.

A VEGF enzyme-linked immunosorbent assay (ELISA) was utilized to determine the effect of the compounds of the present invention on VEGF production of a variety of human cancer cell lines. For the VEGF assay, cells were plated at a concentration of 80,000 cells/well and cultured overnight. Compounds or vehicle (DMSO 0.1%) were then added and the plates were incubated for 72 hours. Supernatant was then collected from each well and frozen in a −80° C. freezer until needed. Cell viability was determined by Neutral Red Assay. VEGF ELISA Kit (R & D, Minneapolis, Minn.) was used to determine the amount of VEGF in the culture supernatants. The ELISA was carried out according to the manufacturer's procedure.

A TF ELISA assay was utilized to determine the effect of the compounds of the present invention on TF production of human cancer cell lines. For the TF assay, cells were plated at a concentration of 80,000 cells/well and cultured overnight. Compounds or vehicle (DMSO 0.1%) were then added and the plates were incubated for 72 hours. Cells were treated with 1% Triton X-100 in PBS and left overnight at 4° C. overnight to solubilize TF. Supernatant was then collected from each well and frozen until needed. IMUBIND Tissue Factor ELISA Kit (American Diagnostica Inc, Greenwich, Conn.) was used to determine TF concentration in each sample. The ELISA was carried out according to manufacturer's procedure.

EXPERIMENTAL

Example 1

Preparation of EF1, EF2, EF3, EF4, EF25, EF31, EF34 Compounds

The compounds of this series were all synthesized by the following procedure: Aqueous NaOH (20 wt %, 15 ml, 75 mmol) was added dropwise to a vigorously stirred solution of hydroxybenzaldehyde (51 mmol) and ketone (25 mmol) in EtOH abs (20 mL). The reaction was stirred at room temperature for 48 hrs, $H_2O$ dist (100 mL) was added, and the purple solution was neutralized by gently bubbling $CO_2$ through it. The precipitating yellow solid was filtered off, washed with $H_2O$ dist and dried under vacuum. The products were purified by recrystallization. A description of each compound obtained by the above process is given below.

1,5-Bis(4-hydroxyphenyl)penta-1,4-dien-3-one (EF1): yellow solid (6%), mp 236° C. (acetone/$H_2O$). $^1$H NMR (400 MHz, $CD_3OD$) δ 7.71 (2H, d, J=16 Hz), 7.58 (4H, d, J=8.8 Hz), 7.07 (2H, d, J=16 Hz), 6.84 (4H, d, J=8.4 Hz). $^{13}$C NMR (100 MHz, $CD_3OD$) δ 191.9, 161.8, 145.3, 131.8, 127.8, 123.6, 117.1. EIHRMS: m/z 266.0943 ($M^+$, $C_{17}H_{14}O_3$ requires 266.0943).

1,5-Bis(2-hydroxyphenyl)penta-1,4-dien-3-one (EF2): yellow solid (75%), mp 155° C. (acetone/$H_2O$). $^1$H NMR (400 MHz, $CD_3OD$) δ 8.09 (2H, d, J=16 Hz), 7.63 (2H, dd, J=8.4 Hz, J=1.6 Hz), 7.31 (2H, d, J=16 Hz), 7.24 (2H, td, J=7.6 Hz, J=1.6 Hz), 6.88 (t, 4H, J=7.2 Hz). $^{13}$C NMR (100 MHz, $CD_3OD$) δ 192.8, 158.9, 141.0, 133.1, 130.2, 126.3, 123.2, 121.0, 117.2. Anal. Calcd for $C_{17}H_{14}O_3$: C, 78.68; H, 5.30. Found: C, 76.56; H, 5.32. EIHRMS: m/z 248.0837 (($M-H_2O)^+$, $C_{17}H_{12}O_2$ requires 248.0837).

1,5-Bis(3-hydroxyphenyl)penta-1,4-dien-3-one (EF3): yellow solid (15%), mp 198-200° C. (acetone/$H_2O$). $^1$H NMR (400 MHz, $CD_3OD$) δ 7.70 (2H, d, J=16 Hz), 7.24 (2H, t, J=7.6 Hz), 7.17 (2H, d, J=16 Hz), 7.17 (2H, d, J=8 Hz), 7.11 (2H, s), 6.73 (2H, dd, J=8 Hz, J=2.4 Hz). $^{13}$C NMR (100 MHz, $CD_3OD$) δ 191.6, 159.3, 145.5, 137.6, 131.2, 126.4, 121.4, 119.1, 115.9. Anal. Calcd for $C_{17}H_{14}O_3$: C, 78.68; H, 5.30. Found: C, 76.41; H, 5.48. EIHRMS: m/z 266.0943 ($M^+$, $C_{17}H_{14}O_3$ requires 266.0943).

2,6-Bis(2-hydroxybenzylidene)cyclohexanone (EF4): yellow solid (70%, recrystallized from acetone/$H_2O$). $^1$H NMR (400 MHz, $CD_3OD$) δ 7.98 (2H, s), 7.32 (2H, dd, J=7.6 Hz, J=1.2 Hz), 7.19 (2H, td, J=7.6 Hz, J=1.2 Hz), 6.86 (4H, m), 2.86 (4H, m), 1.75 (2H, m). $^{13}$C (100 MHz, $CD_3OD$) δ 192.8, 158.2, 137.3, 134.5, 131.5, 124.5, 120.2, 116.6, 29.9, 24.8. Anal. Calcd for $C_{20}H_{18}O_3$: C, 78.41; H, 5.92. Found: C, 78.15; H, 6.03. EIHRMS: m/z 306.1263 ($M^+$, $C_{20}H_{18}O_3$ requires 306.1256).

3,5-Bis(2-hyrdoxybenzylidene)tetrahydro-4-H-pyran-4-one (EF25): yellow solid (60%, recrystallized from acetone/$H_2O$). $^1$H NMR (400 MHz, $CD_3OD$) δ 8.08 (2H, s), 7.24 (2H, td, J=8.4 Hz, J=1.6 Hz), 7.09 (2H, dd, J=7.6 Hz, J=1.6 Hz), 7.90-7.86 (4H, m), 4.84 (4H, d, J=1.6 Hz). $^{13}$C NMR (100 MHz, $CD_3OD$) δ 187.8, 158.5, 133.9, 132.5, 131.9, 123.3, 120.5, 116.8, 70.0. Anal. Calcd for $C_{19}H_{16}O_4$: C, 74.01; H, 5.23. Found: C, 73.23; H, 5.23. EIHRMS: m/z 290.0933 ($M^+$, $C_{19}H_{16}O_4$ requires 290.0943).

2,5-Bis(2-hydroxyphenyl)cyclopentanone (EF31): yellow solid (81%, recrystallized from acetone). $^1$H NMR (400 MHz, $CD_3OD$) δ 8.00 (2H, s), 7.57 (2H, dd, J=8.0 Hz, J=1.2 Hz), 7.22 (2H, td, J=8.0 Hz, J=1.6 Hz), 6.88 (4H, m), 3.06 (4H, s).

3,5-Bis(2-hydroxybenzylidene)1-methyl-4-piperidone (EF34): yellow solid (75%, recrystallized from methanol/$H_2O$). $^1$H NMR (400 MHz, $CD_3OD$) δ 8.11 (2H, s), 7.23 (4H, t, J=7.6 Hz), 6.88 (4H, t, J=8.0 Hz), 3.76 (4H, d, J=1.2 Hz), 2.42 (3H, s). $^{13}$C NMR (100 MHz, $CD_3OD$) δ 188.40, 158.58, 135.09, 133.09, 132.27, 131.64, 123.59, 120.38, 116.87. HREIMS: m/z 303.1259 ($M^+$-$H_2O$, $C_{20}H_{17}NO_2$ requires 303.1259).

Example 2

Preparation of EF8, EF9, EF10, EF23, EF29, EF30, EF33

The compounds of this series were all synthesized by the following procedure: A solution of fluoro-substituted benzaldehyde (5.00 mmol) in ethanol abs. (1 mL) was added at room temperature over a period of 5 min, with stirring, to a solution of NaOH (0.75 mmol) and ketone (acetone, tetrahydro-4-H-pyran-4-one, N-methyl-piperodin-4-one) (2.50 mmol) in a mixture of ethanol abs (7 mL) and $H_2O$ dist. (7 mL). The solution turns yellow immediately, and usually a yellow precipitate starts forming within 10 min (except EF8, where an oil forms). The reaction was stirred at room temperature for 3 hrs., the yellow solid filtered off, washed with water and hexanes and dried under vacuum. The product was obtained in analytically pure form, further purification was only necessary where indicated. A description of each compound obtained by the above process is given below.

1,5-Bis(2-fluorophenyl)penta-1,4-dien-3-one (EF8): yellow solid (50%). $^1$H NMR (400 MHz, $CDCl_3$) δ 7.86 (2H, d, J=16 Hz), 7.63 (2H, td, J=7.6 Hz, J=1.6 Hz), 7.42-7.35 (2H, m), 7.18 (2H, d, J=16 Hz), 7.26-7.10 (4H, m). $^{13}$C NMR (100 MHz, $CDCl_3$) δ 189.2, 161.9 (d, J=253.4 Hz), 136.3 (d, J=2.3 Hz), 132.1 (d, J=9.1 Hz), 129.5 (d, J=2.2 Hz), 127.8 (d, J=6.1 Hz), 124.7 (d, J=3.8 Hz), 123.1 (d, J=11.4 Hz), 116.4 (d, J=22.0 Hz). Anal. Calcd for $C_{17}H_{12}F_2O$: C, 75.55; H, 4.48; F, 14.06. Found: C, 75.30; H, 4.55. EIHRMS: m/z 270.0865 ($M^+$, $C_{17}H_{12}F_2O$ requires 270.0856).

1,5-Bis(2,4-difluorophenyl)penta-1,4-dien-3-one (EF9): yellow solid (72%). $^1$H NMR (300 MHz, $CDCl_3$) δ 7.79 (2H, d, J=16.2 Hz), 7.62 (2H, dd, J=15 Hz, J=8.4 Hz), 7.10 (2H, d, J=16 Hz), 8.85-8.97 (4H, m). $^{13}$C NMR (75 MHz, $CDCl_3$) δ 188.5, 164.8 (dd, J=169.6 Hz, J=12.2 Hz), 161.3 (dd, J=160.3 Hz, J=12.2 Hz), 135.3, 130.7 (q, J=10.0 Hz, J=4.6 Hz), 127.3, 119.5, 112.3 (d, J=21.9 Hz), 104.9 (t, J=25.4 Hz). Anal. Calcd for $C_{17}H_{10}F_4O$: C, 66.67; H, 3.29. Found: C, 66.38; H, 3.41. EIHRMS: m/z 306.0654 ($M^+$, $C_{17}H_{10}OF_4$ requires 306.0668).

1,5-Bis(3,4-difluorophenyl)penta-1,4-dien-3-one (EF10): yellow solid (86%). $^1$H NMR (400 MHz, $CDCl_3$) δ 7.64 (2H, d, J=16 Hz), 7.44 (2H, ddd, J=9.6 Hz, 7.6 Hz, J=2 Hz), 7.32-7.36 (2H, m), 7.18-7.25 (2H, m), 6.96 (2H, d, J=16 Hz). $^{13}$C NMR (100 MHz, $CDCl_3$) δ 180.0, 152.7 (dd, J=105.4 Hz, J=12.9 Hz), 150.2 (dd, J=101.7 Hz, J=12.9 Hz), 141.5, 132.1 (t, J=5.2 Hz), 126.2, 125.5 (q, J=6 Hz, J=3 Hz), 118.2 (d, J=17.5 Hz), 116.7 (d, J=20.5 Hz). Anal. Calcd for $C_{17}H_{10}F_4O$: C, 66.67; H, 3.29. Found: C, 66.54; H, 3.28. EIHRMS: m/z 306.0671 ($M^+$, $C_{17}H_{10}OF_4$ requires 306.0668).

1,5-Bis(2,6-difluorophenyl)penta-1,4-dien-3-one (EF23): yellow solid (91%). $^1$H NMR (400 MHz, CDCl$_3$) δ 7.82 (2H, d, J=16.4 Hz), 7.35 (2H, d, J=16 Hz), 7.33 (2H, td, J=8 Hz, J=2.4 Hz), 6.96 (4H, t, J=8.8 Hz). $^{13}$C NMR (100 MHz, CDCl$_3$) δ 189.5, 162.2 (dd, J=1017.6 Hz, J=29.2 Hz), 131.6 (t, J=10.9 Hz), 131.0 (t, J=8.7 Hz), 129.9, 113.0 (t), 112.1 (d, J=25.6 Hz). Anal. Calcd for C$_{17}$H$_{10}$FO$_4$: C, 66.67; H, 3.29. Found: C, 66.46; H, 3.26, EIHRMS: m/z 306.0657 (M$^+$, C$_{17}$H$_{10}$FO$_4$ requires 306.0668).

3,5-Bis(2-fluorobenzylidene)tetrahydro-4-H-pyran-4-one (EF29): (84%, recrystallized from hot ethanol). $^1$H NMR (400 MHz, CDDl$_3$) δ 7.92 (2H, d, J=1.2 Hz), 7.40-7.36 (2H, m), 7.20-7.18 (4H, m), 7.13 (2H, t, J=9.6 Hz), 4.80 (s, 4H, CH$_2$). $^{13}$C NMR (100 MHz, CDCl$_3$) δ 185.1, 161.0 (d, J=250.7 Hz), 134.8, 131.5 (d, J=8.7 Hz), 131.1 (d, J=2.2 Hz), 129.6 (d, J=3.7 Hz), 124.3 (d, J=3.7 Hz), 122.8 (d, J=13.8 Hz), 116.2 (d, J=21.9 Hz), 68.9 (d, J=5.1 Hz). Anal. Calcd for C$_{19}$H$_{14}$F$_2$O$_2$: C, 73.07; H, 4.52. Found: C, 73.07; H, 4.47. EIHRMS; m/z 312.0950 (M$^+$, C$_{19}$H$_{14}$F$_2$O$_2$ requires 312.0962).

3,5-Bis(2,4-difluorobenzylidene)tetrahydro-4-H-pyran-4-one (EF30): (82%, recryst. from ethanol/H$_2$O). $^1$H NMR (400 MHz, CDCl$_3$) δ 7.85 (2H, s), 7.21-7.14 (1H, m), 6.98-6.87 (2H, m), 4.77 (4H, s). 13C NMR (100 MHz, CDCl$_3$) δ 184.81, 163.95 (dd, J=240 Hz, J=12 Hz), 161.43 (dd, J=265 Hz, J=12 Hz), 134.48, 132.02 (dd, J=9.5 Hz, J=4.3 Hz), 128.62, 119.19, 112.00 (dd, J=3.7 Hz, J=21.9 Hz), 104.85 (t, J=25.5 Hz), 68.81 (d, J=4.4 Hz). Anal. Calcd for C$_{19}$H$_{12}$F$_4$O$_2$: C, 65.52; H, 3.47. Found: C, 65.67; H, 3.43. EIHRMS: m/z 348.0761 (M$^+$, C$_{19}$H$_{14}$F$_2$O$_2$ requires 348.0773).

3,5-Bis(2-fluorobenzylidene)l-methyl-4-piperidone (EF33): (82%, yellow solid). $^1$H NMR (400 MHz, CDCl$_3$) δ 7.90 (2H, s), 7.40-7.33 (2H, m), 7.28 (2H, td, J=7.6 Hz, J=1.2 Hz), 7.18 (2H, td, J=7.6 Hz, J=0.8 Hz), 7.12 (2H, td, J=10.0 Hz, J=0.8 Hz), 3.64 (4H, s), 2.40 (3H, s). $^{13}$C NMR (100 MHz, CDCl$_3$) δ 186.3, 161.1 (d, J=251 Hz), 134.9, 131.1 (d, J=8.1 Hz), 131.0 (d, J=3.0 Hz), 129.7 (d, J=3.6 Hz), 124.1 (d, J=2.9 Hz), 123.4 (d, J=13.9 Hz), 116.1 (d, J=21.8 Hz), 57.2, 45.8. Anal. Calcd for C$_{20}$H$_{17}$F$_2$ON: C, 73.83; H, 5.27; N, 4.30. Found: C, 73.59; H, 5.32; N, 4.39. EIHRMS: m/z 325.1278 (M$_+$, C$_{20}$H$_{17}$F$_2$ON requires 325.1278).

Example 3

Preparation of EF11, EF12, EF13, EF14, EF15

The compounds of this series were all synthesized by the following procedure: Bis-diethylphosphorylmethylsulfide, -sulfoxide and -sulfone were obtained according to literature procedures (*Tetrahedron*, 1992, 48, 8065-8072; *Phosphorus Sulfur* 1981, 10, 369-374). A solution of phosphonate (0.60 mmol) and aldehyde (1.25 mmol) in CH$_2$Cl$_2$ (3 mL) was added to the heterogeneous mixture of 50% aqueous NaOH (2 mL) and CH$_2$Cl$_2$ (2 mL), containing triethylbenzylammonium chloride (TEBA, 0.06 mmol). The reaction was stirred at room temperature over night, the product was extracted from the reaction mixture with CH$_2$Cl$_2$ and purified by column chromatography. A description of each compound obtained by the above process is given below.

3,5-Bis(2-hydroxybenzylidene)-sulfone (EF11): yellow solid (45%, 30% EtOAc/hexanes). $^1$H NMR (400 MHz, CD$_3$OD) δ 7.77 (2H, d, J=15.6 Hz), 7.48 (2H, dd, J=8.4 Hz, J=2.0 Hz), 7.25 (2H, td, J=8.0 Hz, J=2.5 Hz), 7.22 (2H, d, J=15.6 Hz), 6.88-6.84 (4H, m), 4.91 (2H, s-br). $^{13}$C NMR (100 MHz, CD$_3$OD) δ 158.94, 140.21, 133.55, 131.63, 127.84, 121.15, 121.03, 117.23.

3,5-Bisbenzylidenesulfone (EF12): white solid (78%, 20% EtOAc/hexanes). $^1$H NMR (400 MHz, CDCl$_3$) δ 7.65 (2H, d, J=15.2 Hz, H3), 7.53-7.50 (4H, m), 7.44-7.40 (6H m), 6.86 (2H, d, J=15.6 Hz, H2). $^{13}$C NMR (100 MHz, CDCl$_3$) δ 143.7, 132.7, 131.5, 129.3, 128.8, 126.5. Anal. Calcd for C$_{16}$H$_{14}$SO$_2$: C, 71.09; H, 5.22, S, 11.86. Found: C, 70.88; H, 5.21; S, 12.01. EIHRMS: m/z 270.0715 (M$^+$, C$_{16}$H$_{14}$SO$_2$ requires 270.0731).

E,E-3,5-Bisbenzylidenesulfoxide (EF13): white solid (33%, 20% EtOAc, hexanes). $^1$H NMR (300 MHz, CDCl$_3$) δ 7.52-7.46 (4H, m), 7.42-7.35 (6H, m), 7.31 (2H, d, J=15.3 Hz), 6.87 (2H, d, J=15.3 Hz). $^{13}$C NMR (75 MHz, CDCl$_3$) δ 137.0, 133.9, 131.1, 130.0, 129.1, 127.9. Anal. Calcd for C$_{16}$H$_{14}$SO: C, 75.56; H, 5.55, S, 12.60. Found: C, 75.33; H, 5.60; S, 12.60.

E,Z-3,5-Bisbenzylidenesulfoxide (EF14): white solid (15%, 20% EtOAc, hexanes). $^1$H NMR (300 MHz, CDCl$_3$) δ 7.52-7.40 (10H, m), 7.33 (1H, d, J=15.3 Hz), 7.12 (1H, d, J=10.5 Hz), 6.93 (1H, d, J=15.6 Hz), 6.39 (1H, d, J=10.5 Hz). $^{13}$C NMR (75 MHz, CDCl$_3$) δ 138.5, 136.3, 135.5, 134.1, 130.1, 129.8, 129.6, 129.0, 128.8, 127.8. Anal. Calcd for C$_{16}$H$_{14}$SO: C, 75.56; H, 5.55, S, 12.60. Found: C, 75.34; H, 5.54; S, 12.57.

3,5-Bisbenzylidenesulfide (EF15): white solid (20%, 5% EtOAc/hexanes) mixture of E,E and E,Z (ca. 2.5:1). $^1$H NMR (400 MHz, CDCl$_3$) δ 7.40-7.10 (20H, m), 6.79 (2H, d, J=15.6 Hz), 6.76 (1H, d, J=15.6 Hz), 6.62 (2H, d, J=15.6 Hz), 6.61 (1H, d, J=15.6 Hz), 6.53 (1H, J=10.8 Hz), 6.41 (1H, d, J=10.8 Hz). Anal. Calcd for C$_{16}$H$_{14}$S: C, 80.63; H, 5.92; S, 13.45. Found: C, 80.40; H, 5.93; S, 13.39.

Example 4

Preparation of EF16, EF17, EF18, EF27, EF28

The compounds of this series were all synthesized by the following procedure: NaOH (0.10 mmol) was added as a solid to a stirred solution of methoxy-substituted benzaldehyde/anisaldehyde (2.50 mmol) and ketone (acetone, tetrahydro-4-H-pyranone) in EtOH abs (5 mL). A yellow solid started forming within 1 hr. The reaction was stirred at room temperature for 20 hrs, the product filtered off, washed with cold EtOH abs and H$_2$O dist and dried under vacuum. A description of each compound obtained by the above process is given below.

1,5-Bis(2-methoxphenyl)penta-1,4-dien-3-one (EF16): yellow solid (60%). Mp 123-124° C. (EtOH). $^1$H NMR (400 MHz, CDCl$_3$) δ 8.07 (2H, d, J=16 Hz), 7.63 (2H, dd, J=7.6 Hz, J=1.6 Hz), 7.37 (2H, ddd, J=7.2 Hz, J=1.6 Hz, J=1.2 Hz), 7.18 (2H, d, J=16 Hz), 6.99 (2H, t, J=7.6 Hz), 6.93 (2H, d, J=8.4 Hz). $^{13}$C NMR (100 MHz, CDCl$_3$) δ 190.2, 158.7, 138.4, 131.8, 128.9, 126.4, 124.1, 120.9, 111.4, 55.7. Anal. Calcd for C$_{19}$H$_{18}$O$_3$: C, 77.53; H, 6.16. Found: C, 77.26; H, 6.17. EIHRMS: m/z 294.1256 (M$^+$, C$_{19}$H$_{18}$O$_3$ requires 294.1256).

1,5-Bis(3-methoxyphenyl)penta-1,4-dien-3-one (EF17): yellow solid (40%, chromatography using 20% EtOAc/hexanes). $^1$H NMR (300 MHz, CDCl$_3$) δ 7.70 (2H, d, J=15.9 Hz), 7.33 (2H, t, J=7.6 Hz), 7.21 (2H, d, J=7.8 Hz), 7.13 (2H, t, J=2.4 Hz), 7.06 (2H, d, J=15.9 Hz), 6.96 (2H, ddd, J=8.1 Hz, J=2.4 Hz, J=0.9 Hz). $^{13}$C NMR (75 MHz, CDCl$_3$) δ 188.83, 159.96, 143.31, 136.21, 130.03, 125.72, 121.20, 116.46, 113.36, 55.55.

1,5-Bis(4-methoxyphenyl)penta-1,4-dien-3-one (EF18): yellow solid (93%). Mp 129-130° C. (EtOH). $^1$H NMR (300 MHz, CDCl$_3$) δ 7.69 (2H, d, J=15.9 Hz, 3), 7.56 (4H, d, J=9 Hz), 6.95 (2H, d, J=15.6 Hz), 6.92 (4H, d, J=8.7 Hz). $^{13}$C NMR (75 MHz, CDCl$_3$) δ 188.8, 161.5, 142.7, 130.2, 127.7, 126.6, 114.5, 55.6 Anal. Calcd for C$_{19}$H$_{18}$O$_3$: C, 77.53; H, 6.16. Found: C, 77.31; H, 6.217. EIHRMS: m/z 294.1268 (M$^+$, C$_{19}$H$_{18}$O$_3$ requires 294.1256).

3,5-Bis(4-methoxybenzylidene)tetrahydro-4-H-pyran-4-one (EF27): yellow solid (40%). $^1$H NMR (400 MHz, CDCl$_3$) δ 7.79 (2H, s), 7.29 (4H, d, J=8.8 Hz), 6.95 (4H, d, J=9.2 Hz), 4.93 (4H, d, J=1.6 Hz), 3.85 (6H, s). $^{13}$C NMR (100 MHz, CDCl$_3$) δ 185.6, 160.8, 136.2, 132.7, 131.4, 127.7, 114.4, 68.9, 55.6. Anal. Calcd for C$_{21}$H$_{20}$O$_4$: C, 74.98; H, 5.99. Found: C, 74.81; H, 6.01. EIHRMS: m/z 336.1362 (M$^+$, C$_{21}$H$_{20}$O$_4$ requires 336.1361).

3,5-Bis(2-methoxybenzylidene)tetrahydro-4-H-pyran-4-one (EF28): yellow solid (67%). $^1$H NMR (400 MHz, CDCl$_3$) δ 8.09 (2H, s), 7.36 (2H, td, J=8.8 Hz, J=1.6 Hz), 7.07 (2H, dd, J=7.6 Hz, J=1.6 Hz), 6.97 (2H, t, J=7.6 Hz), 6.93 (2H, d, J=8 Hz), 4.81 (4H, d, J=1.6 Hz), 3.87 (6H, s). $^{13}$C NMR (100 MHz, CDCl$_3$) δ 186.0, 158.6, 133.3, 132.5, 131.1, 130.7, 124.1, 120.3, 111.0, 69.1, 55.7. Anal. Calcd for C$_{21}$H$_{20}$O$_4$: C, 74.98; H, 5.99. Found: C, 74.84; H, 5.92. EIHRMS: m/z 336.1370) (M$^+$, C$_{21}$H$_{20}$O$_4$ requires 336.1361).

Example 5

Preparation of EF19, EF20, EF32

The compounds of this series were all synthesized by the following procedure: A solution of substituted dienone (0.69 mmol) in EtOH abs (29 mL) was subject to hydrogenation at 33 psi using Raney Nickel as the catalyst for 4 hrs. Filtration through CELITE and concentration under vacuum yielded the crude product, which was purified by chromatography on silica gel using 25% EtOAc/hexanes. A description of each compound obtained by the above process is given below.

1,5-Bis(2,4-difluorophenyl)-pentan-3-ol (EF19): white solid (92%). $^1$H NMR (300 MHz, CDCl$_3$) δ 7.17-7.09 (2H, m), 6.82-6.72 (4H, m), 3.60 (1H, m), 2.84-2.60 (4H, m), 1.80-1.75 (4H, m), 1.59 (1H, s-br). $^{13}$C NMR (75 MHz, CDCl$_3$) δ 162.9 (dd, J=34.4 Hz, J=12 Hz), 159.7 (dd, J=35 Hz, J=12 Hz), 131.1 (t, J=9 Hz), 124.6 (dd, J=19.7 Hz, J=3.8 Hz), 111.2 (dd, J=20.5 Hz, J=3.4 Hz), 103.8 (t, J=25.7 Hz), 70.6, 38.0, 25.1. Anal. Calcd for C$_{17}$H$_{16}$FO$_4$: C, 65.38; H, 5.16. Found: C, 65.64; H, 5.24. EIHRMS: m/z 312.1137 (M$^+$, C$_{17}$H$_{16}$FO$_4$ requires 312.1137).

1,5-Bis(3,4-difluorophenyl)-pentan-3-ol (EF20): white solid (81%). $^1$H NMR (300 MHz, CDCl$_3$) δ 7.07-6.91 (4H, m), 6.87-6.80 (2H, m), 3.57 (1H, m), 2.77-2.54 (4H, m), 1.73 (4H, t), 1.41 (1H, s-br). $^{13}$C NMR (75 MHz, CDCl$_3$) δ 151.2 (dd, J=107.6 Hz, J=12.5 Hz), 148.0 (dd, J=105.8 Hz, J=12.5 Hz), 138.9 (t), 124.3 (d, J=5.8 Hz), 117.3, 117.1, 70.4, 39.3, 31.5. EIHRMS: m/z 312.1138 (M$^+$, C$_{17}$H$_{16}$FO$_4$ requires 312.1137).

1,5-Bis(2-hydroxyphenyl)-pentan-3-ol (EF32): white solid (45%). $^1$H NMR (300 MHz, CDCl$_3$) δ 7.56 (2H, s-br), 7.09-7.05 (4H, m), 6.87-6.80 (4H, m), 3.54 (1H, m), 2.92-2.84 (2H, m), 2.69-2.62 (2H, m), 1.80-1.71 (4H, m). $^{13}$C NMR (75 MHz, CDCl$_3$) δ 154.11, 130.84, 127.91, 127.77, 121.14, 116.05, 69.28, 37.89, 25.87.

Example 6

Preparation of EF21, EF22

The compounds of this series were all synthesized by the following procedure: PCC (107 mg, 0.50 mmol) was added in one portion at room temperature to a stirred solution of alcohol (103 mg. 0.33 mmol) in CH$_2$Cl$_2$ (5 mL). The reaction was stirred at room temperature for 14 hrs (TLC-analysis, no sm left), filtered over CELITE and concentrated. The crude product was purified by chromatography on silica gel using 20% EtOAc/hexanes. A description of each compound obtained by the above process is given below.

1,5-Bis(2,4-difluorophenyl)-pentan-3-on (EF21): white solid (92%). $^1$H NMR (400 MHz, CDCl$_3$) δ 7.16-7.09 (2H, m), 6.80-6.72 (4H, m), 2.87 (4H, t, J=7.6 Hz), 2.69 (4H, t, J=7.6 Hz). $^{13}$C NMR (100 MHz, CDCl$_3$) δ 208.08, 163.00 (dd, J=48 Hz, J=11.7 Hz), 159.73 (dd, J=49 Hz, J=12 Hz), 131.39, 123.54 (d, J=15.9), 111.17 (dd, J=20.8 Hz, J=3.8 Hz), 103.84 (t, J=25.5 Hz), 42.93, 23.08.

1,5-Bis(3,4-difluorophenyl)-pentan-3-on (EF22): white solid (86%). $^1$H NMR (400 MHz, CDCl$_3$) δ 7.07-7.00 (2H, ddd), 6.98-6.92 (2H, m), 6.87-6.80 (2H, m), 2.84 (4H, t, J=7.2 Hz), 2.68 (4H, t, J=7.2 Hz).

Example 7

Preparation of EF7

EF7 was obtained in a three-step synthesis. To a solution of 2,5-bis(2-hydroxybenzylidene)acetone (800 mg. 3.00 mmol) in DMF (10 mL) was added imidazole (545 mg, 7.56 mmol) and DMAP (10 mg). The bright yellow solution was cooled to 0° C. and tbutyldiphenylchlorosilane (1.75 mL, 6.73 mmol) was added dropwise. After stirring for 30 minutes the cooling bath was removed, and the reaction proceeded at room temperature until no more starting material or monoprotected alcohol were detectable by TLC. (hexanes/EtOAc=2/1, Rf (starting material)=0.17, Rf (mono)=0.44, Rf (di)=0.78). The orange solution was poured into ice water (50 mL) and extracted with ether (3×). The combined organic layers were washed with brine (3×), dried over MgSO$_4$ and concentrated. The crude product was purified by plug chromatography on silica gel (15% EtOAc/hexanes). The product (108%) was obtained as a yellow foam and contains some tbutyldiphenylsilylalcohol. It was used without further purification. $^1$H NMR (400 Mhz, CDCl$_3$) δ 8.48 (2H, d, J=16.0 Hz), 7.75-7.71 (8H, m), 7.66 (2H, dd, J=8.0 Hz, J=2.0 Hz), 7.46-7.35 (12H, m), 7.18 (2H, d, J=16.4 Hz), 6.96 (2H, td), 6.89 (2H, td), 6.50 (2H, dd, J=8.0 Hz, J=1.2 Hz), 1.08 (18H, s). $^{13}$C NMR (100 MHz, CDCl$_3$) δ 189.93, 154.83, 138.24, 135.63, 135.38, 132.35, 130.30, 128.14, 127.92, 127.26, 125.43, 121.54, 120.08, 26.81, 19.88.

Disilylprotected ketone (1.74 g, 2.34 mmol) was dissolved in THF and cooled to −78° C., where CH$_3$Li (1.90 mL, 2.66 mmol, 1.4 M/ether) was added dropwise. After stirring for 10 min the originally bright yellow solution completely cleared, it was quenched with saturated NH$_4$Cl, the layers separated and the aqueous phase extracted with ether. The combined organic layers were washed with brine, dried over MgSO$_4$ and concentrated. The crude product was purified by chromatography on silica gel (10% EtOAc/hexanes). 60%, white foam. $^1$H NMR (400 MHz, CDCl$_3$) δ 7.72 (8H, dd, J=6.4 Hz, J=1.6 Hz), 7.53 (2H, dd, J=7.2 Hz, J=2.4 Hz), 7.41 (4H, m), 7.36-7.32 (10H, m), 6.82 (4H, m), 6.45 (2H, d, J=16.4 Hz), 6.43 (2H, dd, J=7.2 Hz, J=2.8 Hz), 1.67 (3H, s), 1.09 (18H, s). $^{13}$C NMR (100 MHz, CDCl$_3$) δ 152.96, 135.66, 135.33, 132.81, 130.12, 128.33, 128.01, 127.72, 126.42, 123.37, 121.37, 119.62, 74.02, 28.39, 26.73, 19.79.

EF7: Deprotection of the alcohol was carried out with tetrabutylammonium fluoride (2.2 equiv) in THF. The product was obtained after column chromatography on silica gel (30% EtOAc/hexanes) as a white solid (48%). $^1$H NMR (400 MHz, CDCl$_3$) δ 7.32 (1H, dd, J=7.6 Hz, J=1.6 Hz), 7.14-7.07 (2H, m), 7.00 (1H, dd, J=8.0 Hz, J=1.6 Hz), 6.89-6.82 (3H, m), 6.75 (1H, dd, J=8 Hz, J=1.2 Hz), 6.47 (1H, d, J=9.6 Hz), 6.31 (1H, d, J=16.4 Hz), 5.69 (1H, d, J=10 Hz), 5.00 (1H, s-br), 1.66 (3H, s). $^{13}$C NMR (100 MHz, CDCl$_3$) δ 153.1, 153.0, 133.9, 129.5, 129.0, 128.1, 127.8, 126.7, 123.9, 123.7, 121.4, 121.2, 121.1, 116.5, 116.0, 78.0, 27.6. Anal. Calcd for C$_{18}$H$_{16}$O$_2$: C, 81.79; H, 6.10. Found: C, 81.61; H, 6.16. EIHRMS: m/z 264.1150 (M$^+$, C$_{19}$H$_{16}$O$_2$ requires 264.1150).

Example 8

Preparation of EF5

1,5-Bis(2-hydroxyphenyl)penta-1-en-3-ol (EF5): To a solution of 1,5-bis(2-hydroxyphenyl)penta-1,4-dien-3-one (EF1) (109 mg, 0.41 mmol) in THF/methanol (10/1) (2.5 mL) was added NaBH$_4$ (40 mg, 1.30 mmol) in one portion at 0° C. After stirring for 30 min at this temperature the reaction was quenched with H$_2$O dist and cold brine, diluted with Et$_2$O (10 mL) and neutralized by bubbling CO$_2$ through the dark-red solution (color change to pale yellow). The aqueous phase was extracted with ether, the combined ether layers washed with brine, dried over MgSO$_4$ and concentrated. The crude product was purified by chromatography on silica gel using 30% EtOAc/hexanes. The product was obtained as a white solid (66%). $^1$H NMR (300 MHz, CDCl$_3$) δ 7.27 (2H, dd, J=8.0 Hz, J=2.4 Hz), 7.21 (1H, s-br), 7.14-7.06 (3H, m), 6.90-6.83 (3H, m), 6.80-6.74 (2H, m), 6.18 (1H, dd, J=20.8 Hz, J=8.8 Hz), 5.99 (1H, s-br), 4.24 (1H, t-deformed), 3.23 (1H, s-br), 2.86 (1H, m), 2.71 (1H, m), 1.91 (2H, m). $^{13}$C NMR (75 MHz, CDCl$_3$) δ 154.25, 152.96, 132.84, 130.75, 129.03, 127.79, 127.62, 127.46, 125.71, 123.97, 121.12, 121.07, 116.42, 116.22, 72.09, 37.57, 25.76.

Example 9

Preparation of EF6

N-(Methoxy)-1,5-bis(2-hydroxyphenyl)penta-1,4-dien-3-imine (EF6): Methoxyl-amine hydrochloride (30-35 wt % in H$_2$O, 0.30 mL, 1.12 mmol) was added in one portion to a solution of 1,5-bis(2-hydroxyphenyl)penta-1,4-dien-3-one (EF1) in methanol/CHCl$_3$ (2/3) (5 mL). The reaction proceeded at room temperature for 24 hrs, then additional methoxylamine hydrochloride (0.15 mL, 0.56 mmol) was added and the reaction stirred for an additional 24 hrs. After completion (TLC) the solvent was evaporated, the residue dissolved in methanol, stirred with silica gel and purified after concentration by chromatography on silica gel using 30% EtOAc/hexanes. The product was obtained as a pale yellow foam (86%). $^1$H NMR (400 MHz, CDCl$_3$) δ 7.56 (1H, dd, J=8.0 Hz, J=1.6 Hz), 7.48 (1H, dd, J=8.0 Hz, J=1.6 Hz), 7.41 (1H, d, J=16.0 Hz), 7.39 (1H, d, J=16.8 Hz), 7.28 (1H, d, J=16.8 Hz), 7.20-7.13 (2H, m), 6.97-6.90 (2H, m), 6.94 (1H, d, J=16.0 Hz), 6.80 (1H, dd, J=8.0 Hz, J=1.6 Hz), 5.53 (1H, s-br), 5.36 (1H, s-br), 4.02 (3H, s). $^{13}$C NMR (100 MHz, CDCl$_3$) δ 155.43, 153.86, 153.70, 132.28, 130.25, 130.10, 129.71, 128.00, 127.91, 124.16, 123.88, 123.57, 121.40, 121.30, 118.45, 116.37, 116.33, 62.41.

Example 10

Preparation of MD279U and MD279L

A solution of 1,5-bis(3,4-dimethoxyphenyl)penta-1,3-dien-3-one in a mixture of EtOH abs and THF (5/1) was subject to hydrogenation at 50 psi using Raney Nickel as the catalyst for 8 hrs. Filtration through CELITE and concentration under vacuum yielded the crude product, which was purified by chromatography on silica gel using 25% EtOAc/hexanes.

1,5-Bis(3,4-dimethoxyphenyl)penta-3-one (MD279U): 37%, white solid. $^1$H NMR (400 MHz, CDCl$_3$) δ 6.77 (2H, d, J=8.8 Hz), 6.69 (4H, m), 3.86 (6H, s), 3.85 (6H, s), 2.84 (4H, t, J=7.6 Hz), 2.70 (4H, t, J=7.6 Hz). $^{13}$C NMR (100 MHz, CDCl$_3$) δ 209.61, 149.00, 147.50, 133.77, 120.22, 111.82, 111.38, 56.07, 55.98, 45.01, 29.54. R$_f$=0.28 (EtOAc/hexanes=1/2).

1,5-Bis(3,4-dimethoxyphenyl)penta-3-ol (MD279L): 51%, white solid. $^1$H NMR (400 MHz, CDCl$_3$) δ 6.79 (2H, d, J=8.8 Hz), 6.73 (4H, m), 3.87 (6H, s), 3.86 (6H, s), 3.68 (1H, m), 2.78-2.71 (2H, m), 2.63 (2H, ddd, J=14.0 Hz, J=9.2 Hz, J=6.8 Hz), 1.79 (4H, m), 1.58 (1H, s-br). $^{13}$C NMR (100 MHz, CDCl$_3$) δ 149.02, 147.34, 134.80, 120.29, 111.84, 111.39, 71.04.

Example 11

3,5-Bis-(α,α,α-trifluoro-2-toluoylbenzylidene)-piperidin-4-one acetate

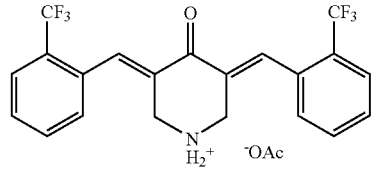

A suspension of 1.76 g (11.49 mmol) of 4-piperidone hydrate, HCl salt, in 60.0 mL of glacial acetic acid was saturated with dry HCl gas and to the resultant solution was added 5.0 g (28.72 mmol) of α,α,α-trifluoro-2-tolualdehyde. The mixture was allowed to stir at room temperature for 72 hrs and then diluted with 50.0 mL of toluene and evaporated under vacuum. The residue was diluted twice more with 50.0 mL portions of toluene and evaporated under vacuum. The gummy residue was suspended in 50 mL of toluene containing 5.0 mL of ethyl acetate, heated briefly to reflux and allowed to cool to room temperature. The solids formed were collected by suction filtration and dried under high vacuum to afford 3.63 g (67%) of a bright yellow solid.

Example 12

3-5-Bis-(pyridinylidene)-piperidin-4-one

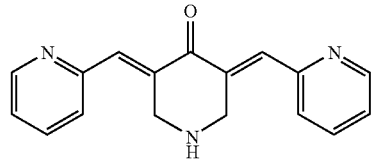

To a solution of 1.00 g (6.52 mmol) of 4-piperidone hydrate, HCl salt, and 1.40 g (13.05 mmol) of 2-pyridine carboxaldehyde in 91 mL of a 0.25M solution of aqueous NaOH (22.82 mmol) was added 0.86 mL of a 25% w/w solution (0.65 mmol) of cetyltrimethylammonium chloride. The mixture was allowed to stir vigorously at room temperature for three hours, diluted with 100 ml of brine and extracted with three 50 mL portions of methylene chloride. The organic phase was dried over anhydrous MgSO4 and concentrated in vacuo. The residue was recrystallized from ethyl acetate to afford 1.25 g (69%) of a red-yellow solid.

Example 13

3,5-Bis-(2-fluoro-3-α,α,α-trifluoromethylbenzylidene)-piperidin-4-one

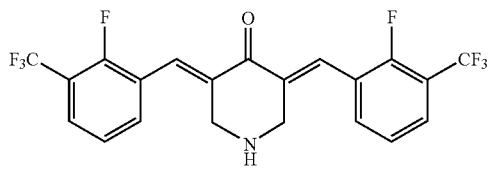

To a solution of 400 mg (2.61 mmol) of 4-piperidone hydrate, HCl salt, and 1.00 g (5.21 mmol) of 2-fluoro-3-α,α,α-trifluoromethylbenzaldehyde in 36 mL of a 0.25M solution of aqueous NaOH (9.11 mmol) was added 0.35 mL of a 25% w/w solution (0.26 mmol) of cetyltrimethylammonium chloride. The mixture was allowed to stir vigorously at room temperature for 48 hours, diluted with 100 ml of brine and extracted with two 50 mL portions of methylene chloride. The organic phase was dried over anhydrous MgSO4 and concentrated in vacuo to afford 1.02 g (86%) of a yellow foam.

Example 14

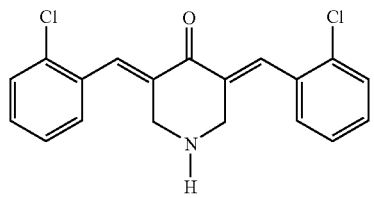

3,5-Bis-(2-chlorobenzylidene)-piperidin-4-one

To a solution of 1.0 g (6.52 mmol) of 4-piperidone hydrate, HCl salt, and 1.88 g (13.37 mmol) of 2-chloro benzaldehyde in 95 mL of a 0.25M solution of aqueous NaOH (22.82 mmol) was added 0.90 mL of a 25% w/w aqueous solution (0.65 mmol) of cetyltrimethylammonium chloride. The mixture was allowed to stir vigorously at room temperature for 48 hours, diluted with 100 ml of brine and extracted with two 35 mL portions of methylene chloride. The organic phase was dried over anhydrous MgSO₄ and concentrated in vacuo. The residue was recrystallized from ethyl acetate to give 0.92 g (41%) of a pale yellow powder.

Example 15

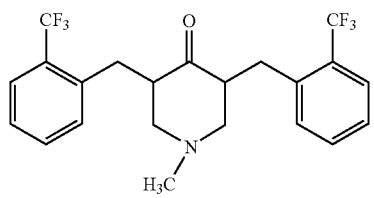

3,5-Bis-(2-α, α, α–trifluoromethylbenzylidiene)-1-methylpiperidin-4-one

To a solution of 1.0 g (8.84 mmol) of 1-methylpiperidine-4-one and 3.08 g (13.37 mmol) of α,α,α-trifluoro-2-tolualdehyde in 88 mL of a 0.25M solution of aqueous NaOH (22.09 mmol) was added 1.16 mL (0.88 mmol) of a 25% w/w aqueous solution of cetyltrimethylammonium chloride. The mixture was allowed to stir vigorously at room temperature for 3 hours, diluted with 100 ml of brine and extracted with three 50 mL portions of methylene chloride. The organic phase was dried over anhydrous MgSO₄ and concentrated in vacuo to give 3.56 g (95%) of a pale yellow powder.

Example 16

3,5-Bis-(2-pyrilidinyldene)-1-methylpiperidin-4-one

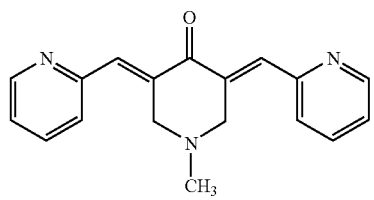

To a solution of 1.0 g (8.84 mmol) of 1-methylpiperidine-4-one and 1.89 g (16.70 mmol) of 2-pyridine carboxaldehyde in 88 mL of a 0.25M solution of aqueous NaOH (22.09 mmol) was added 1.16 mL (0.88 mmol) of a 25% w/w aqueous solution of cetyltrimethylammonium chloride. The mixture was allowed to stir vigorously at room temperature for 3 hours, diluted with 100 ml of brine and extracted with three 50 mL portions of methylene chloride. The organic phase was dried over anhydrous MgSO₄ and concentrated in vacuo to give 2.50 g (97%) of a pale yellow powder.

Example 17

3,5-Bis-(4-pyridinylidene)-1-methylpiperidin-4-one

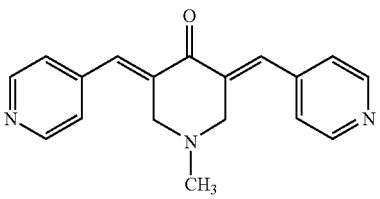

To a solution of 1.0 g (8.84 mmol) of 1-methylpiperidine-4-one and 1.89 g (16.70 mmol) of 4-pyridine carboxaldehyde in 88 mL of a 0.25M solution of aqueous NaOH (22.09 mmol) was added 1.16 mL (0.88 mmol) of a 25% w/w aqueous solution of cetyltrimethylammonium chloride. The mixture was allowed to stir vigorously at room temperature for 3 hours, diluted with 100 ml of brine and extracted with two 60 mL portions of methylene chloride. The organic phase was dried over anhydrous MgSO₄ and concentrated in vacuo to give 2.15 g (84%) of a yellow-orange powder.

Example 18

3,5-Bis-(2,6-difluorobenzylidene)-1-methylpiperidin-4-one

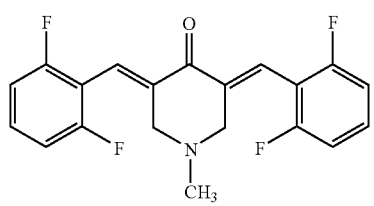

To a solution of 1.0 g (8.84 mmol) of 1-methylpiperidine-4-one and 2.57 g (18.09 mmol) of 2,6-difluoro benzaldehyde in 90 mL of a 0.25M solution of aqueous NaOH (22.59 mmol) was added 1.16 mL (0.88 mmol) of a 25% w/w aqueous solution of cetyltrimethylammonium chloride. The mixture was allowed to stir vigorously at room temperature for 12 hours, diluted with 100 ml of brine and extracted with three 40 mL portions of methylene chloride. The organic phase was dried over anhydrous $MgSO_4$ and concentrated in vacuo. The residue was slurried in 100 ml of boiling ethyl acetate and the insolubles were removed by rapid suction filtration. The filtrate was concentrated in vacuo and recrystallized from ethyl acetate to provide 3.01 g (94%) of a bright yellow solid.

Example 19

3,5-Bis-(2,6-difluorobenzylidene)-tropin-4-one

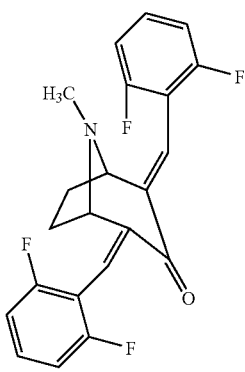

To a solution of 0.50 g (3.59 mmol) of tropinone and 1.05 g (7.39 mmol) of 2,6-difluoro benzaldehyde in 36 mL of a 0.25M solution of aqueous NaOH (9.04 mmol) was added 0.71 mL (0.54 mmol) of a 25% w/w aqueous solution of cetyltrimethylammonium chloride. The mixture was allowed to stir vigorously at room temperature for 4 hours, diluted with 100 ml of brine and extracted with two 25 mL portions of methylene chloride. The organic phase was dried over anhydrous $MgSO_4$ and concentrated in vacuo. The residue was recrystallized from ethyl acetate to provide 840 mg (60%) of a bright yellow solid.

Example 20

3,5-Bis-(2-fluorobenzylidene)-tropin-4-one

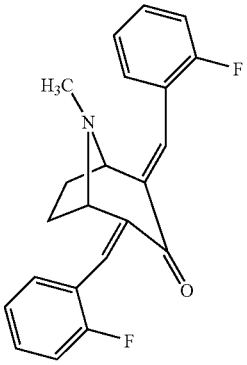

To a solution of 0.50 g (3.59 mmol) of tropinone and 0.914 g (7.36 mmol) of 2-fluoro benzaldehyde in 36 mL of a 0.25M solution of aqueous NaOH (9.04 mmol) was added 0.47 mL (0.36 mmol) of a 25% w/w aqueous solution of cetyltrimethylammonium chloride. The mixture was allowed to stir vigorously at room temperature for 12 hours, diluted with 100 ml of brine and extracted with two 50 mL portions of methylene chloride. The organic phase was dried over anhydrous $MgSO_4$ and concentrated in vacuo. The residue was recrystallized from ethyl acetate to provide

Example 21

3,5-Bis-(2-pyridinylidene)-tropin-4-one

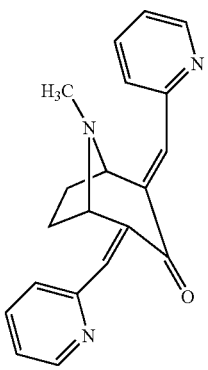

To a solution of 0.75 g (5.39 mmol) of tropinone and 1.18 g (7.39 mmol) of 2-pyridine carboxaldehyde in 54 mL of a 0.25M solution of aqueous NaOH (13.47 mmol) was added 0.71 mL (0.54 mmol) of a 25% w/w aqueous solution of cetyltrimethylammonium chloride. The mixture was allowed to stir vigorously at room temperature for 48 hours, diluted with 150 ml of brine and extracted with three 50 mL portions of methylene chloride. The organic phase was dried over anhydrous $MgSO_4$ and concentrated in vacuo. The residue was recrystallized from ethyl acetate to provide 180 mg (11%) of a tan powder.

Example 22

1,5-Bis-(2,3-dimethyoxyphenyl)-penta-1,4-dien-3-one

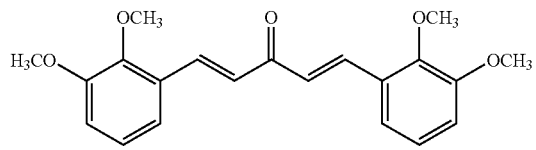

To a solution of 0.5 g (8.61 mmol) of acetone and 2.86 g (17.22 mmol) of 2,3-dimethoxy benzaldehyde in 86 mL of a 0.25M solution of aqueous NaOH (21.59 mmol) was added 2.83 mL (2.15 mmol) of a 25% w/w aqueous solution of cetyltrimethylammonium chloride. The mixture was allowed to stir vigorously at room temperature for 72 hours, diluted with 100 ml of brine and extracted with three 50 mL portions of methylene chloride. The organic phase was dried over anhydrous MgSO$_4$ and concentrated in vacuo. The residue was recrystallized from ethyl acetate to provide 1.99 g (65%) of a bright yellow solid.

Example 23

1,5-Bis-(2,3-methylenedioxyphenyl)-penta-1,4-dien-3-one

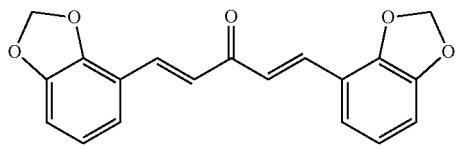

To a solution of 0.19 g (3.27 mmol) of acetone and 1.00 g (6.66 mmol) of 2,3-methylenedioxy benzaldehyde in 35 mL of a 0.25M solution of aqueous NaOH (8.79 mmol) was added 0.65 mL (0.49 mmol) of a 25% w/w aqueous solution of cetyltrimethylammonium chloride. The mixture was allowed to stir vigorously at room temperature for 2 hours, at which point it was diluted with 15 mL of 95% ethanol, and stirring was continued for an additional 2 hours. The solution was saturated with sodium chloride and extracted with two 35 mL portions of methylene chloride. The organic phase was dried over anhydrous MgSO$_4$ and concentrated in vacuo. The residue was recrystallized from ethyl acetate to provide 1.03 g (98%) of a yellow solid.

Example 24

1,5-Bis-(4-dimethylaminophenyl)-penta-1,4-dien-3-one

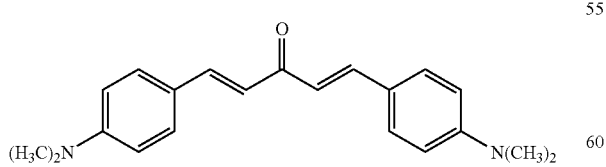

To a solution of 1.0 g (17.22 mmol) of acetone and 5.26 g (35.30 mmol) of 4-dimethylamino benzaldehyde in 172 mL of a 0.25M solution of aqueous NaOH (43.05 mmol) was added 2.26 mL (1.72 mmol) of a 25% w/w aqueous solution of cetyltrimethylammonium chloride. The mixture was allowed to stir vigorously at room temperature for 72 hours, diluted with 100 ml of brine and extracted with two 75 mL portions of methylene chloride. The organic phase was dried over anhydrous MgSO$_4$ and concentrated in vacuo. The residue was recrystallized from ethyl acetate to provide 1.21 g (22%) of a dark red powder.

Example 25

1,5-Bis-(2,6-dimethoxyphenyl)-penta-1,4-dien-3-one

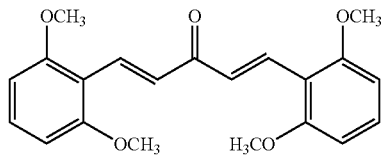

To a solution of 0.25 g (4.31 mmol) of acetone and 1.47 g (8.85 mmol) of 2,6-dimethoxy benzaldehyde in 43 mL of a 0.25M solution of aqueous NaOH (10.80 mmol) was added 0.57 mL (0.43 mmol) of a 25% w/w aqueous solution of cetyltrimethylammonium chloride. The mixture was allowed to stir vigorously at room temperature for 72 hours, diluted with 100 ml of brine and extracted with two 75 mL portions of methylene chloride. The organic phase was dried over anhydrous MgSO$_4$ and concentrated in vacuo. The residue was recrystallized from ethyl acetate to provide 1.10 g (72%) of a yellow powder.

Example 26

1,5-Bis-(2,3-difluorophenyl)-penta-1,4-dien-3-one

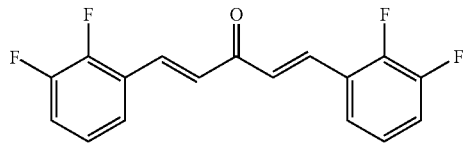

To a solution of 0.5 g (8.61 mmol) of acetone and 2.51 g (17.65 mmol) of 2,3-difluoro benzaldehyde in 86 mL of a 0.25M solution of aqueous NaOH (21.52 mmol) was added 1.13 mL (0.86 mmol) of a 25% w/w aqueous solution of cetyltrimethylammonium chloride. The mixture was allowed to stir vigorously at room temperature for 48 hours, at which point it was diluted with 100 ml of brine and extracted with two 75 mL portions of methylene chloride. The organic phase was dried over anhydrous MgSO$_4$ and concentrated in vacuo. The residue was recrystallized from ethyl acetate to provide 110 mg (4%) of a yellow powder.

Example 27

(E)-3-(2-fluorobenzylidenyl)indolin-2-one

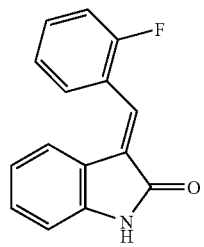

To a solution containing 2.0 g (15.02 mmol) of 2-oxindole and 2.05 g (16.52 mmol) of 2-fluoro benzaldehyde in 30 mL of abs. ethanol was added 190 mg (2.25 mmol) piperidine and the mixture was refluxed for 12 hrs. The mixture was allowed to cool to room temperature and the solids formed were collected by suction filtration and washed with two 25 mL portions of cold abs. ethanol. The recovered material was dried under high vacuum for 12 hrs. to afford 3.22 g (90%) of a bright yellow powder.

Example 28

(E)-3-(2-pyridinylidenyl)indolin-2-one

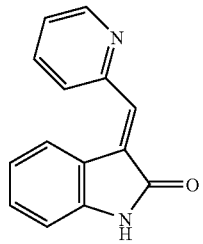

To a solution containing 2.0 g (15.02 mmol) of 2-oxindole and 1.77 g (16.52 mmol) of 2-pyridine carboxaldehyde in 30 mL of abs. Ethanol was added 192 mg (2.25 mmol) piperidine and the mixture was refluxed for 12 hrs. The mixture was allowed to cool to room temperature and the solids formed were collected by suction filtration and washed with two 25 mL portions of cold abs. ethanol. The recovered material was dried under high vacuum for 12 hrs to afford 2.82 g (84%) of a pale red powder.

Example 29

(E)-3-(2,3-difluorobenzylidenyl)indolin-2-one

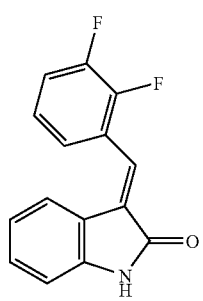

To a solution containing 2.0 g (15.02 mmol) of 2-oxindole and 2.20 g (16.52 mmol) of 2,3-difluoro benzaldehyde in 30 mL of abs. ethanol was added 192 mg (2.25 mmol) piperidine and the mixture was refluxed for 12 hrs. The mixture was allowed to cool to room temperature and the solids formed were collected by suction filtration and washed with two 25 mL portions of cold abs. ethanol. The recovered material was dried under high vacuum for 12 hrs.

Example 30

1,3-Bis-(2-fluorobenzylidene)indan-2-one

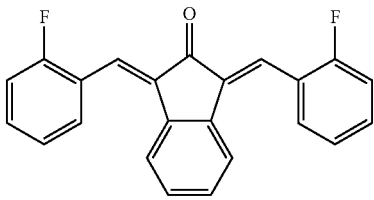

A solution of 1.88 g (15.13 mmol) of 2-fluorobenzaldehyde in 3.0 mL of abs. ethanol was added over a period of 5 min to a solution containing 1.00 g (7.57 mmol) of 2-indanone and 90 mg (2.27 mmol) of NaOH in 40 mL of a 1:1 mixture of abs.ethanol and water at room temperature. The mixture was allowed to stir for 12 hrs and solids formed were collected by suction filtration and washed with cold ethanol and dried under high vacuum.

Example 31

3,5-Bis-(2-fluorobenzylidene)-piperidin-4-one-acetate

EF24

4-Piperidone hydrochloride monohydrate (307 mg, 2.00 mmol) was suspended in glacial acetic acid (8 mL) and saturated with HCl gas at room temperature. To the resulting clear solution 2-fluorobenzaldehyde (0.59 mL, 5.60 mmol) was added and the reaction allowed to stand at room temperature for 48 h. The forming yellow crystals were filtered off, washed with EtOH abs and dried under vacuum. Further purification was not necessary.

Yellow crystals (91%). $^1$H NMR (400 MHz, $d_6$-DMSO) δ 10.11 (1H, s-br), 7.90 (2H, s), 7.57 (2H, qd, J=7.6 Hz, J=1.6 Hz), 7.51 (2H, td, J=8.0 Hz, J=1.2 Hz), 7.37 (4H, q, J=10.0 Hz), 4.37 (4H, s), 3.60-3.20 (1H, s-br), 1.91 (3H, s). $^{13}$C NMR (100 MHz, $d_6$-DMSO) δ 181.95, 172.04, 160.33 (d, J=249 Hz), 132.57 (d, J=9 Hz), 131.81 (d, J=4 Hz), 131.05, 129.86, 124.96 (d, J=3 Hz), 121.49 (d, J=13 Hz), 116.1 (d, J=21 Hz), 43.79, 21.11. HREIMS: m/z 311.1123 (M$^+$-HOAc, $C_{19}H_{15}NOF_2$ requires 311.1122).

Example 32

Cell Viability and VEGF/TF Inhibition Analysis

As described above, the effect of the compounds of the present invention on Neutral Red uptake, VEGF production, and TF production was measured for a variety of human cancer cell lines. Some of this data is also summarized in FIGS. 1-5. Note that, as applied to compounds EF4, MD6 and MD10 in the figures, the term "known" means that the listed compounds have appeared in the literature, but without any suggestion that those compounds exhibit anti-angiogenic properties or usefulness as a cancer treatment. Table 1 below lists the results for selected curcumin analogs of the present invention in comparison to the results for curcumin and other known chemotherapeutic and anti-angiogenic agents for RPMI-7951 cells.

TABLE 1

Characteristics of Selected Novel Curcumin Analogs in the Human Melanoma Cell Line RPMI-7951 as Measured by the Neutral Red, VEGF ELISA[a] and TF ELISA[d] Assays; Comparison with Melanoma and Anti-Angiogenesis Agents

| Compound | Neutral Red Uptake, %[b] | | VEGF[c] ELISA | | TF[c] ELISA | |
|---|---|---|---|---|---|---|
| | 5 μM | 20 μM | 5 μM | 20 μM | 5 μM | 20 μM |
| DMSO (0.1%) | | 100 | | 3713 | | 7054 |
| Curcumin | 100 | 14 | 3989 | 714 | 7974 | 1026 |
| Series I | | | | | | |
| MD6 | 97 | 6 | 2826 | 273 | 1753 | ND |
| MD10 | 82 | 6 | 1585 | 315 | 1793 | ND |
| EF-1 | 92 | 8 | 1923 | 234 | ND | ND |
| EF-2 | 46 | 7 | 1295 | 84 | 1009 | ND |
| EF-3 | 77 | 8 | 2092 | 230 | ND | ND |
| EF-4 | 98 | 4 | 2159 | 199 | ND | ND |
| EF-8 | 97 | 8 | 2208 | 319 | ND | ND |
| EF-9 | 88 | 11 | 1868 | 705 | ND | ND |
| EF-10 | ND | 8 | ND | 257 | ND | ND |
| Series II | | | | | | |
| MD279L | 100 | 100 | 2235 | 1603 | 5791 | 5858 |
| MD279U | 100 | 100 | 2511 | 779 | 7200 | 5316 |
| EF-15 | 100 | 100 | 2361 | 894 | 7506 | 7663 |
| Melanoma Chemotherapeutic Agents | | | | | | |
| Decabazine | 100 | 100 | 1136 | 1531 | ND | ND |
| Cisplatin | 100 | 100 | | | | |
| Known Anti-angiogenic Agent | | | | | | |
| Thalidomide | 100 | 100 | 1810 | 2827 | ND | ND |

[a]Measurement of the extent of suppression of the vascular endothelial growth factor (VEGF) vs. DMSO control and curcumin.
[b]% of control.
[c]In concentration units of pg/ml/well.
[d]Measurement of the extent of suppression of tissue factor (TF) vs. DMSO control and curcumin.

As indicated in the table and accompanying figures, two series of analogs were discovered. The Series I analogs proved to inhibit VEGF production and simultaneously inhibit cell growth for several cancer cell lines. Some of the compounds within this group were also more efficacious than TAXOL in preventing growth of a human breast cancer cell line and more potent than curcumin and CISPLATIN in inhibiting proliferation of normal human and transformed murine VECs.

The Series II analogs, which include EF15, EF19-22, MD279L and MD279U, selectively blocked VEGF production without causing cell death. These compounds were also not cytotoxic to normal or malignant VECs.

These results indicate that the analogs of the present invention can directly inhibit tumor and vascular endothelial cell growth as well as shut down the production of VEGF which is vital for tumor-induced angiogenesis. Thus, the results suggest that the novel Series I analogs are potential anti-cancer/anti-angiogenic agents, while the Series II compounds are promising anti-angiogenic drugs with little toxicity to normal VECs.

Example 33

TABLE 2

Vascular Endothelial Growth Factor (VEGF) Production by Human Melanoma Cell Line, RPMI-7951 measured by VEGF ELISA assay

| Concentrations of compounds | Cell Viability | | VEGF | | | |
|---|---|---|---|---|---|---|
| | 5 μM (%) | 20 μM (%) | 5 μM (pg/ml) | (%) | 20 μM (pg/ml) | (%) |
| DMSO (0.1%) | 100 | 100 | 4197 | 100 | 4197 | 100 |
| Curcumin | 105 | 47 | 4111 | 98 | 221 | 5 |
| Our synthetic curcumin analogs which inhibit VEGF production and cell growth. | | | | | | |
| EF-1 | 98 | 43 | 2573 | 61 | 0 | 0 |
| EF-2 | 68 | 42 | 1522 | 36 | 0 | 0 |
| EF-3 | 88 | 43 | 2827 | 67 | 0 | 0 |
| EF-4 | 102 | 38 | 2920 | 70 | 0 | 0 |
| EF-5 | n.d. | 84 | n.d. | n.d. | n.d. | 41 |
| EF-6 | n.d. | 72 | n.d. | n.d. | n.d. | 45 |
| EF-7 | n.d. | 78 | n.d. | n.d. | n.d. | 27 |
| EF-8 | 94 | 54 | 2276 | 54 | 35 | 1 |
| EF-9 | 92 | 70 | 1925 | 46 | 595 | 14 |
| EF-10 | n.d. | 54 | n.d. | n.d. | 217 | 5 |
| EF-11 | n.d. | 93 | n.d. | n.d. | n.d. | 51 |
| EF-12 | n.d. | 92 | n.d. | n.d. | n.d. | 70 |
| EF-13 | n.d. | 92 | n.d. | n.d. | n.d. | 53 |
| EF-14 | n.d. | 86 | n.d. | n.d. | n.d. | 36 |
| EF-25 | 12 | n.d. | 216* | 21 | n.d. | n.d. |
| A231L | n.d. | 77 | n.d. | n.d. | n.d. | 25 |
| A231U | n.d. | 80 | n.d. | n.d. | n.d. | 34 |
| A232 | n.d. | 78 | n.d. | n.d. | n.d. | 40 |
| A239 | n.d. | 86 | n.d. | n.d. | n.d. | 40 |
| Our synthetic curcumin analogs which inhibit VEGF production, but not cell growth. | | | | | | |
| EF-15 | 112 | 111 | 1187 | 28 | 938 | 22 |
| A279L | 110 | 109 | 904 | 22 | 0 | 0 |
| A279U | 112 | 113 | 1197 | 28 | 1179 | 18 |
| Drugs Currently in Market | | | | | | |
| **Decarbazine | 91 | 99 | 1171 | 28 | 1293 | 31 |
| ***Thalidomide | 105 | 97 | 1865 | 44 | 2387 | 57 |
| Other Tested Compounds | | | | | | |
| MD6 | 101 | 42 | 3200 | 76 | 30 | 1 |
| MD10 | 91 | 42 | 1866 | 44 | 0 | 0 |
| BA 3 | 93 | 102 | 4860 | 116 | 2035 | 48 |
| BA 4 | 90 | 84 | 4708 | 112 | 3348 | 80 |

Values are a mean of the duplicate assays.
*DMSO (0.1%): VEGF 1045 pg/ml = 100%
**Decarbazine: Chemotherapeutic drug currently used for treatment of human melanoma.
***Thalidomide: Anti-angiogenic drug currently under clinical trial.
n.d.: not done

Example 34

TABLE 3

Vascular Endothelial Growth Factor (VEGF) and Tissue Factor (TF) Production by Human Prostate Cancer Cell lines, DU-145 and PC-3 measured by VEGF ELISA and TF ELISA, respectively. All compounds are used at 20 μM and DMSO (solvent control), 0.1% at a final concentration.

| | VEGF | | TF | |
|---|---|---|---|---|
| | DU-145 pg/ml | PC-3 pg/ml | DU-145 pg/ml | PC-3 pg/ml |
| DMSO | 18760 ± 2633 (100%) | 2103 ± 100 (100%) | 7699 ± 406 (100%) | 203 ± 6 (100%) |
| Curcumin | 17957 ± 1910 (96%) | 2088 ± 103 (99%) | 7134 ± 301 (93%) | 138 ± 10 (68%) |

TABLE 3-continued

Vascular Endothelial Growth Factor (VEGF) and Tissue Factor (TF) Production by Human Prostate Cancer Cell lines, DU-145 and PC-3 measured by VEGF ELISA and TF ELISA, respectively
All compounds are used at 20 μM and DMSO (solvent control), 0.1% at a final concentration.

|  | VEGF | | TF | |
|---|---|---|---|---|
|  | DU-145 pg/ml | PC-3 pg/ml | DU-145 pg/ml | PC-3 pg/ml |
| Our synthetic curcumin analogs | | | | |
| A | 26565 ± 9818 (142%) | 1729 ± 59 (82%) | n.d. | n.d. |
| B | 15321 ± 5607 (82%) | 2168 ± 279 (99%) | n.d. | n.d. |
| C | 20559 ± 9224 (110%) | 1734 ± 397 (82%) | n.d. | n.d. |
| EF-1 | 19616 ± 4624 (105%) | 325 ± 75 (15%) | 12879 ± 149 (167%) | 107 ± 9 (53%) |
| EF-2 | 7516 ± 1915 (40%) | 26 ± 44 (1%) | 5540 ± 364 (72%) | 73 ± 10 (36%) |
| EF-3 | 25901 ± 620 (138%) | 917 ± 261 (44%) | 6687 ± 188 (87%) | 140 ± 8 (69%) |
| EF-4 | 10274 ± 4467 (55%) | 48 ± 83 (2%) | 5180 ± 420 (67%) | 33 ± 7 (16%) |
| A231U | 27875 ± 4446 (149%) | 984 ± 349 (47%) | n.d. | n.d. |
| A271a | 24190 ± 2160 (129%) | 1196 ± 438 (57%) | n.d. | n.d. |
| MD6 | 18428 ± 3377 (98%) | 1820 ± 283 (87%) | n.d. | n.d. |
| MD10 | 7830 ± 2262 (42%) | 611 ± 248 (29%) | 5886 ± 332 (76%) | 0 ± 0 (0%) |
| BA-8 | 40883 ± 6639 (218%) | 1648 ± 229 (78%) | n.d. | n.d. |

Values are a mean of the triplicate assays and S.D.
n.d.: not done
As you can see, DU-145 has a 20-fold higher level of VEGF production than PC-3 cells. This level is seen only one other cell line, MDA-MB-231 breast cancer cell. Greater the VEGF and TF production, higher concentration of compounds will be required to inhibit the same percentage, e.g., effect of E-2 on DU-145 and PC-3 cells.
Both cell lines do not produce basic FGF (bFGF) at all.

Example 35

TABLE 4

Vascular Endothelial Growth Factor (VEGF) Production by Human Prostate Cancer Cell Lines, DU-145 & PC-3 measured by VEGF ELISA assay
All compounds are used at 20 μM and DMSO (solvent control), 0.1% at a final concentration.

|  | DU-145 VEGF | | PC-3 VEGF | |
|---|---|---|---|---|
|  | (pg/ml) | (%) | pg/ml | (%) |
| DMSO | 18760 ± 2633 | 100 | 2103 ± 100 | 100 |
| Curcumin | 17957 ± 1910 | 96 | 2088 ± 103 | 99 |
| Our synthetic curcumin analogs | | | | |
| A | 26565 ± 9818 | 142 | 1729 ± 59 | 82 |
| B | 15321 ± 5607 | 82 | 2168 ± 279 | 103 |
| C | 20559 ± 9224 | 110 | 1734 ± 397 | 82 |
| EF-1 | 19616 ± 4624 | 105 | 325 ± 75 | 15 |
| EF-2 | 7516 ± 1915 | 40 | 26 ± 44 | 1 |
| EF-3 | 25901 ± 620 | 149 | 917 ± 261 | 44 |
| EF-4 | 10274 ± 4467 | 55 | 48 ± 83 | 2 |
| EF-5 | 20140 ± 2874 | 107 | 2748 ± 416 | 131 |
| A231L | 27927 ± 4466 | 149 | 1687 ± 250 | 80 |
| A231U | 27875 ± 4446 | 149 | 984 ± 349 | 47 |
| A232 | 25308 ± 4722 | 135 | 1955 ± 437 | 93 |
| A239 | 27229 ± 2148 | 145 | 1678 ± 293 | 80 |
| A271a | 24190 ± 2160 | 129 | 1196 ± 438 | 57 |
| A272 | 24155 ± 4635 | 129 | 1864 ± 339 | 89 |
| A277a | 27403 ± 3143 | 146 | 2007 ± 30 | 95 |
| A277b | 27124 ± 1346 | 145 | 1868 ± 38 | 89 |
| MD6 | 18428 ± 3377 | 98 | 1820 ± 283 | 87 |
| MD10 | 7830 ± 2262 | 42 | 611 ± 248 | 29 |
| BA-8 | 40883 ± 6639 | 218 | 1648 ± 229 | 78 |

As you can see, DU-145 has a 20-fold higher level of VEGF production than PC-3 cells. This level is seen only one other cell line, MDA-MB-231 breast cancer cell. Greater the VEGF production, higher concentration of compounds will be required to inhibit the same percentage, e.g., effect of E-2 on DU-145 and PC-3 cells. Both cell lines do not produce basic FGF at all.

Values are a mean of the triplicate assays and S.D.

Example 36

TABLE 5

Tissue Factor (TF) Production by Human Melanoma Cell Line, RPMI-7951 measured by TF ELISA assay

|  | TF | | | | | |
|---|---|---|---|---|---|---|
| Concentrations | 1 μM | | 5 μM | | 20 μM | |
| of compounds | (pg/ml) | (%) | (pg/ml) | (%) | (pg/ml) | (%) |
| DMSO (0.1%) | 7054 | 100 | 7054 | 100 | 7054 | 100 |
| Curcumin | n.d. |  | 8871 | 126 | 1026 | 15 |
| Our synthetic curcumin analogs | | | | | | |
| EF-2 | n.d. |  | 5780 | 82 | 1009 | 14 |
| EF-15 | n.d. |  | 7506 | 106 | 7663 | 109 |
| EF-32 | n.d. |  | n.d. |  | 8654 | 123 |
| A231U | n.d. |  | 5473 | 78 | 5981 | 85 |
| A279L | n.d. |  | 5791 | 82 | 5858 | 83 |
| A279U | n.d. |  | 7200 | 102 | 5316 | 75 |
| MD6 | 6400 | 91 | 1753 | 25 | n.d. |  |
| MD10 | 7966 | 113 | 1793 | 25 | n.d. |  |
| BA-1 | n.d. |  | n.d. |  | 6669 | 95 |
| BA-3 | n.d. |  | n.d. |  | 2088 | 30 |
| BA-4 | n.d. |  | 7043 | 100 | 2120 | 30 | n.d.: not done. Values are a mean of the duplicate assays.

Example 37

TABLE 6

Tissue Factor (TF) Production by Human Breast Cancer Cell Line, MDA-MB-231 measured by TF ELISA assay

| Concentrations of compounds | TF | | | | | | | |
|---|---|---|---|---|---|---|---|---|
| | 0.5 μM | | 5 μM | | 10 μM | | 20 μM | |
| | (pg/ml) | (%) | (pg/ml) | (%) | (pg/ml) | (%) | (pg/ml) | (%) |
| DMSO (0.1%) | 45753 | 100 | 45753 | 100 | 45753 | 100 | 45753 | 100 |
| Curcumin | n.d. | | 45814 | 100 | 44727 | 98 | n.d. | |
| Our synthetic curcumin analogs | | | | | | | | |
| EF-2 | 37697 | 82 | n.d. | | n.d. | | n.d. | |
| A279L | n.d. | | n.d. | | n.d. | | 42601 | 93 |
| A279L | n.d. | | n.d. | | n.d. | | 42190 | 92 |
| EF-15 | n.d. | | n.d. | | n.d. | | 46394 | 101 | n.d.: not done. Values are a mean of the duplicate assays.

Example 38

A number of the compounds of the present invention were screened for activity using the NCI Anti-Tumor Screen. The results are given in Tables 7-9 below. Sixty human tumor cell lines were treated for 48 hours with 10-fold dilutions of compounds at a minimum of five concentrations (0.01 μM-100 μM). Sulforhodamine B (SRB) assay was used to calculate cell viability or growth. GI50 refers to the concentration at which the drug inhibits tumor cell growth by 50%. LC50 refers to the concentration at which the drug causes 50% tumor cell death. EF 24 and EF 25 represent the average of three separate experiments.

TABLE 7

Median Growth Inhibitory Concentration (GI50, μM) of Compounds in NCI Anti-Tumor Screen

| Panel/Cell Line | COMPOUNDS | | | | | | | | | |
|---|---|---|---|---|---|---|---|---|---|---|
| | EF4 | EF7 | EF9 | EF11 | EF15 | EF19 | EF24 | EF25 | Curcumin | CISPLATIN |
| Leukemia | | | | | | | | | | |
| CCRF-CEM | 1.4 | 12.5 | 3.1 | 22.0 | 41.5 | 18.2 | 0.2 | 0.3 | 3.2 | 0.2 |
| HL-60 (TB) | 1.9 | 17.7 | 4.2 | 21.3 | 49.9 | 18.1 | 0.4 | 1.1 | 7.9 | 0.1 |
| K-562 | 2.5 | 14.9 | 3.5 | 27.4 | 78.5 | 19.0 | 0.3 | 0.6 | 3.2 | 1.0 |
| MOLT-4 | 2.2 | 7.7 | 9.3 | 19.7 | >100 | 2.6 | 0.5 | 0.4 | 5.0 | 0.3 |
| RPMI-8226 | 0.6 | 14.8 | 2.4 | 18.2 | 49.8 | 21.7 | 0.2 | 0.2 | 2.0 | 0.5 |
| SR | 1.6 | 15.2 | 1.2 | 21.5 | 52.0 | 22.7 | 0.1 | 0.2 | 3.2 | 0.1 |
| Non-Small Cell Lung Cancer | | | | | | | | | | |
| A549 | 2.6 | 14.9 | 8.9 | 38.7 | >100 | 18.0 | 1.9 | 2.5 | 12.6 | 0.8 |
| EKVX | 2.3 | 17.3 | 11.8 | 30.6 | 64.0 | 17.5 | 0.9 | 1.4 | 15.8 | 1.6 |
| HOP-62 | 2.9 | 16.3 | 16.6 | 83.3 | >100 | 18.0 | 0.7 | 1.5 | 4.0 | 0.3 |
| HOP-92 | 2.8 | 12.7 | 16.3 | 23.5 | >100 | 17.5 | 3.0 | 2.4 | ND | 0.6 |
| NCI-H226 | 19.0 | 18.7 | 24.3 | >100 | >100 | 19.9 | 3.6 | 2.2 | 20.0 | 0.8 |
| NCI-H23 | 1.8 | 17.6 | 12.3 | 35.8 | >100 | 22.8 | 0.9 | 1.7 | 5.0 | 0.1 |
| NCI-H322M | 2.7 | 16.9 | 16.7 | 36.5 | >100 | 20.3 | 1.4 | 1.9 | 15.8 | 1.3 |
| NCI-H460 | 2.3 | 17.6 | 12.7 | 30.7 | >100 | 17.9 | 81.0 | 1.2 | 7.9 | 0.1 |
| NCI-H522 | 2.9 | 16.2 | 13.4 | 33.3 | 69.9 | 18.2 | 0.9 | 0.9 | 5.0 | 0.8 |
| Colon Cancer | | | | | | | | | | |
| COLO 205 | 2.0 | 17.5 | 7.6 | 39.6 | >100 | 17.5 | 0.8 | 2.0 | 12.6 | 4.0 |
| HCC-2998 | 1.7 | 18.4 | 3.3 | 20.5 | 31.6 | 17.7 | 1.1 | 1.5 | 3.2 | 0.1 |
| HCT-116 | 2.2 | 17.6 | 1.9 | 36.8 | >100 | 17.8 | 0.2 | 0.8 | 3.2 | 1.3 |
| HCT-15 | 2.2 | 17.2 | 4.9 | 42.6 | 49.1 | 24.8 | 0.2 | 0.7 | 4.0 | 1.6 |
| HT29 | 2.2 | 17.8 | 4.1 | 45.9 | 46.1 | 17.9 | 0.3 | 2.0 | 5.0 | 1.3 |
| KM12 | 1.6 | 17.1 | 2.3 | 19.1 | 55.7 | 17.6 | 0.2 | 0.3 | 5.0 | 2.0 |
| SW-620 | 2.7 | 16.2 | 3.2 | 32.5 | 79.8 | 17.7 | 0.2 | 0.5 | 4.0 | 0.8 |
| CNS Cancer | | | | | | | | | | |
| SF-268 | 3.0 | 19.8 | 13.7 | 24.6 | >100 | 21.5 | 0.6 | 1.4 | 6.3 | 0.2 |
| SF-295 | 3.4 | 15.5 | 14.2 | 53.8 | 80.9 | 18.7 | 85.0 | 1.7 | 7.9 | 0.3 |
| SF-539 | 2.0 | 17.3 | 2.6 | 39.9 | >100 | 16.9 | 0.3 | 0.5 | 3.2 | 0.4 |

TABLE 7-continued

Median Growth Inhibitory Concentration (GI50, μM) of Compounds in NCI Anti-Tumor Screen

| Panel/Cell Line | COMPOUNDS | | | | | | | | | |
|---|---|---|---|---|---|---|---|---|---|---|
| | EF4 | EF7 | EF9 | EF11 | EF15 | EF19 | EF24 | EF25 | Curcumin | CISPLATIN |
| SNB-19 | 3.2 | 17.5 | 14.7 | 48.0 | >100 | 16.1 | 0.7 | 2.2 | 7.9 | 1.0 |
| SNB-75 | 2.0 | 11.8 | 11.2 | 20.3 | 98.8 | 19.0 | 2.0 | 1.8 | 6.3 | 0.6 |
| U251 | 2.0 | 16.1 | 2.1 | 35.7 | 95.1 | 17.4 | 0.2 | 0.7 | 5.0 | 0.4 |
| Melanoma | | | | | | | | | | |
| LOX IMVI | 2.2 | 17.2 | 3.4 | 40.3 | >100 | 20.0 | 0.2 | 0.2 | 2.5 | 0.3 |
| MALME-3M | 2.3 | 17.5 | 17.8 | 40.7 | >100 | 18.0 | 2.3 | 1.9 | 12.6 | 0.2 |
| M14 | 1.9 | 15.7 | 4.1 | 33.9 | >100 | 18.3 | 1.2 | 1.8 | 4.0 | 0.3 |
| SK-MEL-2 | 2.4 | 16.8 | 14.5 | 24.0 | 31.7 | 18.4 | 2.6 | 2.0 | 15.8 | 1.3 |
| SK-MEL-28 | 2.9 | 17.4 | 18.6 | 42.5 | 83.7 | 17.1 | 2.1 | 2.4 | 5.0 | 0.8 |
| SK-MEL-5 | 1.6 | 15.5 | 12.1 | 23.2 | 53.9 | 17.1 | 1.3 | 1.5 | 7.9 | 0.5 |
| UACC-257 | 2.9 | 16.9 | 16.0 | 29.8 | 55.4 | 17.9 | 1.8 | 1.6 | 12.6 | 1.0 |
| UACC-62 | 1.5 | 12.2 | 13.9 | 21.3 | 66.7 | 15.1 | 1.6 | 1.7 | 6.3 | 0.3 |
| Ovarian Cancer | | | | | | | | | | |
| IGROV1 | 2.9 | 15.9 | 3.8 | 35.9 | >100 | 17.2 | 0.8 | 0.8 | 7.9 | 0.6 |
| OVCAR-3 | 3.7 | 15.6 | 14.1 | 41.8 | >100 | 17.9 | 1.1 | 0.9 | 6.3 | 1.0 |
| OVCAR-4 | 2.5 | 14.1 | 15.2 | 28.7 | >100 | 17.4 | 0.7 | 2.0 | 10.0 | 0.3 |
| OVCAR-5 | 2.6 | 16.7 | 20.0 | 89.2 | >100 | 18.5 | 1.3 | 1.7 | 15.8 | 1.3 |
| OVCAR-8 | 2.9 | 17.0 | 3.4 | 47.1 | >100 | 18.0 | 0.4 | 0.8 | 7.9 | 1.0 |
| SK-OV-3 | 6.7 | 16.6 | 15.4 | >100 | >100 | 18.5 | 1.7 | 2.4 | 7.9 | 1.3 |
| Renal Cancer | | | | | | | | | | |
| 786-0 | 2.3 | 16.4 | 3.5 | 41.3 | >100 | 17.0 | 0.2 | 0.4 | 3.2 | 0.3 |
| A498 | 2.2 | 17.2 | 2.4 | 34.2 | 23.3 | 16.3 | 0.9 | 1.3 | 15.8 | 2.0 |
| ACHN | 3.3 | 15.7 | 16.5 | 41.0 | >100 | 17.8 | 1.1 | 1.5 | 12.6 | 0.5 |
| CAKI-1 | 3.1 | 14.3 | 15.0 | 29.2 | >100 | 21.8 | 0.8 | 1.8 | 12.6 | 0.3 |
| RXF 393 | 0.5 | 11.0 | 2.3 | 39.0 | 23.5 | 18.8 | 0.6 | 0.6 | 3.2 | 0.8 |
| SN12C | 2.3 | 15.2 | 17.1 | 34.2 | >100 | 17.4 | 1.0 | 1.4 | 7.9 | 1.0 |
| TK-10 | 3.0 | 17.4 | 17.9 | 41.2 | >100 | 17.4 | 3.1 | 2.2 | 15.8 | 1.3 |
| UO-31 | 1.6 | 13.5 | 9.6 | 28.4 | 96.8 | 18.2 | 0.6 | 1.2 | 12.6 | 0.8 |
| Prostate Cancer | | | | | | | | | | |
| PC-3 | 2.1 | 17.2 | 4.8 | 34.9 | >100 | 17.5 | 0.3 | 0.5 | 7.9 | 1.6 |
| DU-145 | 1.4 | 16.4 | 2.1 | 29.9 | >100 | 18.1 | 0.7 | 1.2 | 15.8 | 0.4 |
| Breast Cancer | | | | | | | | | | |
| MCF-7 | 2.7 | 18.0 | 3.0 | 28.7 | 44.6 | 17.7 | 0.2 | 0.3 | 3.2 | 0.4 |
| NCI/ADR-RES | 2.7 | 19.3 | 30.7 | 86.1 | >100 | 25.3 | 0.9 | 1.6 | 7.9 | 0.8 |
| MDA-MB-231 | 3.5 | 19.8 | 14.1 | 25.6 | >100 | 22.4 | 1.3 | 1.9 | 20.0 | 3.2 |
| HS 578T | 5.1 | 22.4 | 9.9 | 52.1 | >100 | 21.9 | 1.0 | 5.1 | 10.0 | 1.3 |
| MDA-MB-435 | 1.8 | 17.5 | 3.2 | 31.4 | 61.2 | 17.1 | 0.6 | 1.0 | 3.2 | 1.6 |
| MDA-N | 1.6 | 16.1 | 2.9 | 36.9 | 67.8 | 16.9 | 0.5 | 1.0 | 2.5 | 0.8 |
| BT-549 | 2.4 | 17.1 | 6.5 | 32.9 | >100 | 17.9 | 0.7 | 1.5 | 5.0 | 1.3 |
| T-47D | 1.7 | 7.7 | 4.4 | 24.7 | 18.5 | 15.5 | 1.3 | 1.3 | 7.9 | 2.0 |
| Mean | 2.4 | 15.8 | 7.2 | 34.7 | 75.9 | 17.8 | 0.7 | 1.1 | 6.7 | 0.7 |

ND—Not Determined

As shown, EF4, EF24 and EF 25 exhibited a lower GI50 than the chemotherapeutic agent CISPLATIN for several cell types.

TABLE 8

Median Lethal Concentration (LC50, μM) of Compounds in NCI Anti-Tumor Screen

| Panel/Cell Line | COMPOUNDS | | | | | | | |
|---|---|---|---|---|---|---|---|---|
| | EF4 | EF7 | EF9 | EF19 | EF24 | EF25 | Curcumin | CISPLATIN |
| Leukemia | | | | | | | | |
| CCRF-CEM | 59.1 | 79.5 | >100 | 72.3 | 70.9 | >100 | <100 | 39.8 |
| HL-60 (TB) | 53.5 | 76.0 | >100 | 66.8 | >100 | >100 | <100 | 50.1[#] |
| K-562 | 91.4 | 70.7 | >100 | 90.1 | 75.4 | 91.8 | <100 | 50.1 |
| MOLT-4 | 69.5 | 64.7 | >100 | 75.6 | 66.2 | >100 | 79.4 | 50.1 |
| RPMI-8226 | >100 | 92.7 | 95.6 | >100 | 54.9 | 70.9 | <100 | 50.1 |
| SR | >100 | 76.8 | 77.9 | 82.6 | 68.2 | 76.3 | 79.4 | 50.1 |

TABLE 8-continued

Median Lethal Concentration (LC50, μM) of Compounds in NCI Anti-Tumor Screen

| Panel/Cell Line | EF4 | EF7 | EF9 | EF19 | EF24 | EF25 | Curcumin | CISPLATIN |
|---|---|---|---|---|---|---|---|---|
| Non-Small Cell Lung Cancer | | | | | | | | |
| A549 | >100 | 53.3 | 71.0 | 65.8 | 89.4 | 71.8 | 79.4 | 50.1 |
| EKVX | 37.2 | 56.6 | 49.1 | 57.7 | 9.4 | 24.2 | 79.4 | 50.1 |
| HOP-62 | 69.1 | 63.1 | 60.7 | 58.7 | 28.8 | 37.2 | 63.1 | 50.1 |
| HOP-92 | 41.4 | 54.9 | 70.4 | 59.3 | 23.3 | 35.4 | ND | 50.1 |
| NCI-H226 | >100 | 78.8 | >100 | 75.7 | 48.3 | 58.0 | <100 | 50.1 |
| NCI-H23 | 9.4 | 62.9 | 62.3 | 96.8 | 5.3 | 12.9 | <100 | 50.1 |
| NCI-H322M | 42.3 | 56.0 | 55.6 | 59.2 | 17.0 | 32.2 | 63.1 | 50.1 |
| NCI-H460 | 40.2 | 66.8 | 60.9 | 57.5 | 50.1 | 38.9 | 63.1 | 39.8 |
| NCI-H522 | >100 | >100 | 57.1 | 75.4 | 22.9 | 14.1 | 79.4 | 50.1 |
| Colon Cancer | | | | | | | | |
| COLO 205 | 8.7 | 55.9 | 52.8 | 55.9 | 8.0 | 33.4 | 63.1 | 50.1 |
| HCT-2998 | 5.9 | 56.8 | 32.2 | 56.1 | 5.0 | 5.3 | 31.6 | 19.9 |
| HCT-116 | 13.2 | 57.6 | 7.7 | 56.3 | 1.8 | 11.1 | 50.1 | 50.1 |
| HCT-15 | >100 | 68.9 | 64.7 | >100 | 13.6 | 16.1 | 79.4 | 50.1 |
| HT29 | 29.1 | 60.6 | 41.9 | 62.6 | 57.3 | 67.5 | <100 | 50.1 |
| KM12 | 6.5 | 55.5 | 14.6 | 56.1 | 3.4 | 10.7 | 63.1 | 50.1 |
| SW-620 | 76.3 | 65.9 | 62.6 | 63.7 | 4.4 | 75.3 | 79.4 | 50.1 |
| CNS Cancer | | | | | | | | |
| SF-268 | 53.2 | >100 | >100 | 85.3 | 55.6 | 43.3 | <100 | 50.1 |
| SF-295 | 79.5 | 55.1 | 58.8 | 69.7 | 20.6 | 35.0 | 50.1 | 50.1 |
| SF-539 | 24.7 | 55.7 | 23.1 | 55.3 | 7.6 | 16.8 | 31.6 | 50.1 |
| SNB-19 | 42.3 | 55.9 | 58.8 | 57.3 | 19.3 | 37.3 | 63.1 | 50.1 |
| SNB-75 | 21.5 | 49.0 | 48.8 | 57.5 | 8.8 | 14.0 | 50.1 | 50.1 |
| U251 | 18.5 | 54.4 | 12.9 | 55.8 | 0.8 | 5.8 | 50.1 | 39.8 |
| Melanoma | | | | | | | | |
| LOX IMVI | >100 | 73.4 | 67.6 | 74.4 | 6.7 | 3.6 | <100 | 50.1 |
| MALME-3M | 24.3 | 68.8 | 73.4 | 59.6 | 25.2 | 19.3 | 50.1 | 39.8 |
| M14 | 13.2 | 54.0 | 48.6 | 68.7 | 27.7 | 19.4 | 50.1 | 50.1 |
| SK-MEL-2 | 25.3 | 57.0 | 58.9 | 57.0 | 19.5 | 12.6 | 79.4 | 50.1 |
| SK-MEL-28 | 33.8 | 62.9 | 61.1 | 55.6 | 33.1 | 6.6 | 50.1 | 50.1 |
| SK-MEL-5 | 5.7 | 53.7 | 53.1 | 55.5 | 6.4 | 6.6 | 50.1 | 7.9 |
| UACC-257 | 57.8 | 55.2 | 62.1 | 56.3 | 13.5 | 8.2 | 50.1 | 50.1 |
| UACC-62 | 6.1 | 49.6 | 52.8 | 53.2 | 4.5 | 14.4 | 50.1 | 15.8 |
| Ovarian Cancer | | | | | | | | |
| IGROV1 | 43.9 | 60.9 | 46.2 | 55.6 | 7.1 | 14.5 | 79.4 | 50.1 |
| OVCAR-3 | 40.7 | 54.5 | 52.1 | 59.3 | 16.2 | 23.5 | 63.1 | 50.1 |
| OVCAR-4 | 18.4 | 53.1 | 61.6 | 65.1 | 17.2 | 23.3 | <100 | 39.8 |
| OVCAR-5 | 55.9 | 58.4 | 63.3 | 61.1 | 9.2 | 8.4 | 79.4 | 50.1 |
| OVCAR-8 | >100 | 86.4 | 85.3 | 67.3 | 31.3 | 23.0 | 79.4 | 50.1 |
| SK-OV-3 | 63.6 | 56.2 | 53.7 | 65.9 | 12.8 | 26.9 | 50.1 | 50.1 |
| Renal Cancer | | | | | | | | |
| 786-O | 15.9 | 54.8 | 49.6 | 55.4 | 1.6 | 32.6 | 39.8 | 50.1 |
| A498 | 16.2 | 55.6 | 23.0 | 54.7 | 3.4 | 6.0 | 63.1 | 50.1 |
| ACHN | 32.7 | 54.0 | 54.8 | 56.3 | 5.6 | 18.2 | 63.1 | 50.1 |
| CAKI-1 | >100 | 52.3 | 93.4 | 67.8 | 27.2 | 53.7 | 50.1 | 50.1 |
| RXF 393 | 30.8 | 49.2 | 17.9 | 58.4 | 3.6 | 4.6 | 50.1 | 50.1 |
| SN12C | 21.5 | 54.4 | 62.3 | 55.9 | 5.4 | 12.0 | 63.1 | 50.1 |
| TK-10 | 22.6 | 55.9 | 56.5 | 56.3 | 27.8 | 24.6 | 63.1 | 50.1 |
| UO-31 | 6.2 | 51.3 | 49.5 | 56.6 | 4.5 | 68.1 | 50.1 | 25.1 |
| Prostate Cancer | | | | | | | | |
| PC-3 | 28.6 | 55.6 | 41.0 | 56.7 | 7.2 | 24.8 | 63.1 | 50.1 |
| DU-145 | 7.0 | 54.8 | 29.0 | 56.6 | 5.4 | 20.1 | 63.1 | 50.1 |
| Breast Cancer | | | | | | | | |
| MCF-7 | 44.1 | 65.9 | 42.2 | 57.1 | 5.0 | 44.7 | <100 | 50.1 |
| NCI/ADR-RES | >100 | >100 | >100 | >100 | 60.6 | 71.0 | <100 | 50.1 |
| MDA-MB-231 | >100 | 74.6 | 57.7 | 66.3 | 9.1 | 17.2 | <100 | 50.1 |
| HS 578T | >100 | >100 | >100 | >100 | 81.4 | 72.3 | <100 | 50.1 |
| MDA-MB-435 | 8.0 | 56.0 | 35.9 | 55.6 | 7.4 | 16.3 | 39.8 | 39.8 |
| MDA-N | 20.2 | 56.9 | 33.2 | 55.2 | 5.6 | 20.0 | 31.6 | 39.8 |
| BT-549 | 26.1 | 56.8 | 47.3 | 64.7 | 4.7 | 13.6 | 39.8 | 50.1 |
| T-47D | 50.8 | 55.4 | 56.1 | 68.9 | 51.9 | 92.9 | <100 | 50.1 |
| Mean | 33.9 | 61.7 | 52.5 | 64.6 | 13.2 | 24.2 | 66.0 | 46.0 |

EF4, EF9, EF24, and EF25 exhibited a lower LC50 than the chemotherapeutic agent CISPLATIN for several cell types.

Human tumor and endothelial cell lines were treated for 72 hours with compounds at a minimum of four concentrations between 0.1 μM-40 μM. Neutral Red assay was used to calculate cell viability. The numbers in Table 9 are representative of at least three separate experiments.

TABLE 9

Median Growth Inhibitory Concentration (GI50, μM) of Compounds in Emory Laboratory Cell Screen

| Panel/Cell Line | COMPOUNDS | | | | | | | | | |
|---|---|---|---|---|---|---|---|---|---|---|
| | EF2 | EF4 | EF25 | EF34 | MD6 | MD10 | MD283 | MD286 | MD287 | Curcumin |
| Melanoma | | | | | | | | | | |
| RPMI 7951 | 0.8 | 3.6 | 0.6 | ND | 1.9 | 2.2 | 1.4 | 1.0 | 0.7 | 6.3 |
| Breast Cancer | | | | | | | | | | |
| MDA-MB-231 | 1.5 | ND | 0.8 | 0.8 | ND | ND | 1.8 | ND | ND | 11.6 |
| MDA-MB-435 | 3.3 | ND | 1.8 | ND | ND | ND | 1.9 | ND | ND | 16.3 |
| HUVECS | 1.7 | ND | 1.5 | ND | 3.8 | 14.0 | 3.1 | 2.3 | 6.8 | 25 |
| Mean | 1.8 | 3.6 | 1.2 | 0.8 | 2.9 | 8.1 | 2.1 | 1.7 | 3.8 | 14.8 |

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A pharmaceutical formulation comprising a compound of the formula:

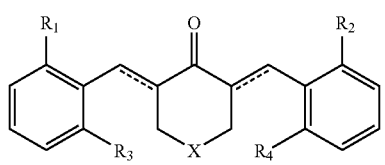

wherein:
the dashed lines indicate the presence of optional double bonds;
X is O, S, or $NR_5$,
$R_1$ and $R_2$ are independently selected from the group consisting of halogen, hydroxyl, alkoxy, $CF_3$, alkyl, substituted alkyl, alkenyl, alkynyl, cycloalkyl, substituted cycloalkyl, aryl, substituted aryl, alkaryl, arylalkyl, heteroaryl, substituted heteroaryl, heterocycle, substituted heterocycle, amino, alkylamino, dialkylamino, carboxylic acid, carboxylic ester, carboxamide, nitro, cyano, azide, alkylcarbonyl, acyl, and trialkylammonium;
$R_3$ and $R_4$ are independently selected from the group consisting of H, halogen, hydroxyl, alkoxy, $CF_3$, alkyl, substituted alkyl, alkenyl, alkynyl, cycloalkyl, substituted cycloalkyl, aryl, substituted aryl, alkaryl, arylalkyl, heteroaryl, substituted heteroaryl, heterocycle, substituted heterocycle, amino, alkylamino, dialkylamino, carboxylic acid, carboxylic ester, carboxamide, nitro, cyano, azide, alkylcarbonyl, acyl, and trialkylammonium;
$R_5$ is selected from the group consisting of H, alkyl, substituted alkyl, acyl, alkoxycarbonyl, aminocarbonyl, alkylaminocarbonyl, and dialkylaminocarbonyl; or
a pharmaceutically acceptable salt thereof; and
a pharmaceutically acceptable carrier.

2. The pharmaceutical formulation of claim 1, wherein X is $NR_5$.

3. The pharmaceutical formulation of claim 2, wherein $R_5$ is a H.

4. The pharmaceutical formulation of claim 2, wherein $R_1$ and $R_2$ are independently selected from the group consisting of halogen, hydroxyl, and alkoxy.

5. The pharmaceutical formulation of claim 2, wherein $R_1$ and $R_2$ are hydroxyl.

6. The pharmaceutical formulation of claim 2, wherein $R_1$ and $R_2$ are independently selected from the group of halogen.

7. The pharmaceutical formulation of claim 2, wherein $R_1$ and $R_2$ are F.

8. The pharmaceutical formulation of claim 1, wherein X is O.

9. The pharmaceutical formulation of claim 8, wherein $R_1$ and $R_2$ are independently selected from the group consisting of halogen, hydroxyl, and alkoxy.

10. The pharmaceutical formulation of claim 1, wherein X is S.

11. The pharmaceutical formulation of claim 10, wherein $R_1$ and $R_2$ are independently selected from the group consisting of halogen, hydroxyl, and alkoxy.

12. The pharmaceutical formulation of claim 1, wherein $R_1$ and $R_2$ are independently selected from the group consisting of halogen, hydroxyl, and alkoxy.

13. A method of treating cancerous tissue in a subject, comprising administering to the subject an effective amount of a compound of the formula

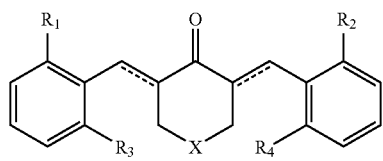

wherein:
the dashed lines indicate the presence of optional double bonds;

X is O, S, or NR$_5$,

R$_1$ and R$_2$ are independently selected from the group consisting of halogen, hydroxyl, alkoxy, CF$_3$, alkyl, substituted alkyl, alkenyl, alkynyl, cycloalkyl, substituted cycloalkyl, aryl, substituted aryl, alkaryl, arylalkyl, heteroaryl, substituted heteroaryl, heterocycle, substituted heterocycle, amino, alkylamino, dialkylamino, carboxylic acid, carboxylic ester, carboxamide, nitro, cyano, azide, alkylcarbonyl, acyl, and trialkylammonium;

R$_3$ and R$_4$ are independently selected from the group consisting of H, halogen, hydroxyl, alkoxy, CF$_3$, alkyl, substituted alkyl, alkenyl, alkynyl, cycloalkyl, substituted cycloalkyl, aryl, substituted aryl, alkaryl, arylalkyl, heteroaryl, substituted heteroaryl, heterocycle, substituted heterocycle, amino, alkylamino, dialkylamino, carboxylic acid, carboxylic ester, carboxamide, nitro, cyano, azide, alkylcarbonyl, acyl, and trialkylammonium; and R$_5$ is selected from the group consisting of H, alkyl, substituted alkyl, acyl, alkoxycarbonyl, aminocarbonyl, alkylaminocarbonyl, and dialkylaminocarbonyl; or a pharmaceutically acceptable salt thereof;

wherein said cancerous tissue is selected from the group consisting of breast cancer, colon cancer, prostate cancer, skin cancer, leukemia, non-small cell lung cancer, CNS cancer, ovarian cancer, and renal cancer.

14. The method of claim 13, wherein the effective amount comprises an amount sufficient to inhibit VEGF production in the cancerous tissue.

15. The method of claim 13, wherein the effective amount comprises an amount sufficient to inhibit TF production in the cancerous tissue.

16. The method of claim 13, wherein said administering step comprises administering an effective amount of the compound in a pharmaceutically acceptable carrier.

17. The method of claim 13, wherein X is NR$_5$.

18. The method of claim 17, wherein R$_5$ is a H.

19. The method of claim 17, wherein R$_1$ and R$_2$ are independently selected from the group consisting of halogen, hydroxyl, and alkoxy.

20. The method of claim 17, wherein R$_1$ and R$_2$ are hydroxyl.

21. The method of claim 17, wherein R$_1$ and R$_2$ are independently selected from the group of halogen.

22. The method of claim 17, wherein R$_1$ and R$_2$ are F.

23. The method of claim 13, wherein X is O.

24. The method of claim 23, wherein R$_1$ and R$_2$ are independently selected from the group consisting of halogen, hydroxyl, and alkoxy.

25. The method of claim 13, wherein X is S.

26. The method of claim 25, wherein R$_1$ and R$_2$ are independently selected from the group consisting of halogen, hydroxyl, and alkoxy.

27. The method of claim 13, wherein R$_1$ and R$_2$ are independently selected from the group consisting of halogen, hydroxyl, and alkoxy.

28. A method of treating an inflammatory skin condition in a subject, comprising administering to the subject an effective amount of a compound of the formula

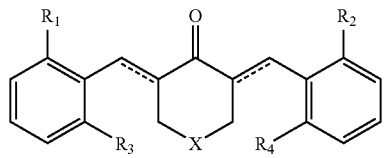

wherein:

the dashed lines indicate the presence of optional double bonds;

X is O, S, or NR$_5$,

R$_1$ and R$_2$ are independently selected from the group consisting of halogen, hydroxyl, alkoxy, CF$_3$, alkyl, substituted alkyl, alkenyl, alkynyl, cycloalkyl, substituted cycloalkyl, aryl, substituted aryl, alkaryl, arylalkyl, heteroaryl, substituted heteroaryl, heterocycle, substituted heterocycle, amino, alkylamino, dialkylamino, carboxylic acid, carboxylic ester, carboxamide, nitro, cyano, azide, alkylcarbonyl, acyl, and trialkylammonium;

R$_3$ and R$_4$ are independently selected from the group consisting of H, halogen, hydroxyl, alkoxy, CF$_3$, alkyl, substituted alkyl, alkenyl, alkynyl, cycloalkyl, substituted cycloalkyl, aryl, substituted aryl, alkaryl, arylalkyl, heteroaryl, substituted heteroaryl, heterocycle, substituted heterocycle, amino, alkylamino, dialkylamino, carboxylic acid, carboxylic ester, carboxamide, nitro, cyano, azide, alkylcarbonyl, acyl, and trialkylammonium; and R$_5$ is selected from the group consisting of H, alkyl, substituted alkyl, acyl, alkoxycarbonyl, aminocarbonyl, alkylaminocarbonyl, and dialkylaminocarbonyl; or a pharmaceutically acceptable salt thereof.

29. The method of claim 28, wherein the inflammatory skin condition is dermatitis.

30. The method of claim 28, wherein the inflammatory skin condition is related to skin cancer.

* * * * *